US012773649B2

(12) United States Patent
Rubin

(10) Patent No.: US 12,773,649 B2
(45) Date of Patent: Oct. 27, 2026

(54) SYSTEMS AND METHODS FOR REHABILITATING COFFEE BEANS AND BREWED COFFEE

(71) Applicant: True Essence Foods Inc., Indianapolis, IN (US)

(72) Inventor: Matthew Rubin, Indianapolis, IN (US)

(73) Assignee: TRUE ESSENCE FOODS INC., Indianapolis, IN (US)

( * ) Notice: Subject to any disclaimer, the term of this patent is extended or adjusted under 35 U.S.C. 154(b) by 56 days.

(21) Appl. No.: 17/918,003

(22) PCT Filed: Jul. 27, 2021

(86) PCT No.: PCT/US2021/043269
§ 371 (c)(1),
(2) Date: Feb. 14, 2023

(87) PCT Pub. No.: WO2022/026438
PCT Pub. Date: Feb. 3, 2022

(65) Prior Publication Data
US 2024/0017187 A1 Jan. 18, 2024

Related U.S. Application Data

(60) Provisional application No. 63/093,045, filed on Oct. 16, 2020, provisional application No. 63/156,588,
(Continued)

(51) Int. Cl.
*B01D 3/10* (2006.01)
*A23F 5/10* (2006.01)
(Continued)

(52) U.S. Cl.
CPC .............. *B01D 3/106* (2013.01); *A23F 5/105* (2013.01); *A23F 5/16* (2013.01); *B01D 3/001* (2013.01);
(Continued)

(58) Field of Classification Search
CPC .......... B01D 3/001; B01D 3/42; B01D 3/106; C12F 3/06; C12G 3/08; A23F 5/105;
(Continued)

(56) References Cited

U.S. PATENT DOCUMENTS 4,015,022 A * 3/1977 Emich ........................ A23F 5/16 426/432
4,215,150 A 7/1980 Kurzhals
(Continued)

FOREIGN PATENT DOCUMENTS

CA 1168089 5/1984
CA 1168089 A 5/1984
(Continued)

OTHER PUBLICATIONS

Quarta et al. Furfurals removal from roasted coffee powder by vacuum treatment_2011, p. 610-614 (Year: 2011).*
(Continued)

*Primary Examiner* — Erik Kashnikow
*Assistant Examiner* — Luis Eugenio Diou Berdecia
(74) *Attorney, Agent, or Firm* — QUARLES & BRADY LLP

(57) ABSTRACT

A method for rehabilitating coffee beans or brewed coffee, including placing a quantity of coffee solution or roasted coffee beans in a pressure-controllable environment, decreasing the pressure of the pressure-controllable environment to about 75 Torr, holding the pressure of the pressure-controllable environment at about 75 Torr for a first predetermined period of time, removing unwanted congeners, such as ethyl acetate, from the coffee solution or roasted coffee beans to yield a treated coffee, and removing treated coffee from the pressure-controllable environment.

31 Claims, 28 Drawing Sheets

Related U.S. Application Data filed on Mar. 4, 2021, provisional application No. 63/156,517, filed on Mar. 4, 2021, provisional application No. 63/209,487, filed on Jun. 11, 2021.

(51) Int. Cl.

| | |
|---|---|
| ***A23F 5/16*** | (2006.01) |
| ***B01D 3/00*** | (2006.01) |
| ***B01D 3/42*** | (2006.01) |
| ***C07C 29/84*** | (2006.01) |
| ***C12F 3/06*** | (2006.01) |
| ***C12G 3/08*** | (2006.01) |

(52) U.S. Cl.

CPC ................ *B01D 3/42* (2013.01); *C07C 29/84* (2013.01); *C12F 3/06* (2013.01); *C12G 3/08* (2013.01)

(58) Field of Classification Search

CPC ...... A23F 5/16; A23F 5/00; A23F 5/20; A23F 5/04; C07C 29/84; A23N 12/125; A23N 12/10; A23N 12/08; A23N 12/12; A23L 5/30

USPC .......... 426/492, 404, 466, 406, 242; 99/292, 99/454, 472, 286, 289 D, 462, 461, 463, 99/464, 466, 471, 477, 501, 503, 507, 99/574, 580, 593, 597, 598, 599, 611, 99/617, 621, 625, 627, 628, 629, 630

See application file for complete search history.

(56) References Cited

U.S. PATENT DOCUMENTS

| | | | | |
|---|---|---|---|---|
| 4,279,937 | A | 7/1981 | Strobel | |
| 4,347,321 | A | 8/1982 | Lionelle | |
| 4,352,829 | A | 10/1982 | Noyes et al. | |
| 4,486,453 | A | 12/1984 | Morrison, Jr. et al. | |
| 5,035,908 | A * | 7/1991 | Arora | A23F 5/36 426/594 |
| 5,211,816 | A * | 5/1993 | Youngner | B01D 1/0094 202/205 |
| 5,458,739 | A | 10/1995 | Boucher | |
| 5,820,820 | A * | 10/1998 | Pierce | A23B 2/90 426/233 |
| 6,019,034 | A | 2/2000 | Ford, Sr. | |
| 6,626,092 | B2 | 9/2003 | Tarlow | |
| 7,285,300 | B1 * | 10/2007 | Allington | A23N 12/08 426/523 |
| 9,200,243 | B2 | 12/2015 | Mosier | |
| 10,428,298 | B1 * | 10/2019 | Salzman | C12G 3/08 |
| 11,772,009 | B2 | 10/2023 | Rubin et al. | |
| 2002/0192342 | A1 * | 12/2002 | Horn | A23B 2/80 426/524 |
| 2013/0243922 | A1 | 9/2013 | Lynn | |
| 2014/0287110 | A1 * | 9/2014 | Mosier | C12H 3/02 99/277.2 |
| 2015/0230492 | A1 * | 8/2015 | Day, Jr. | B65B 29/00 426/232 |
| 2018/0360064 | A1 * | 12/2018 | Elsby | A23F 5/04 |
| 2019/0274329 | A1 * | 9/2019 | Mora | A23F 5/26 |

FOREIGN PATENT DOCUMENTS

| | | | | |
|---|---|---|---|---|
| CH | 140081 | A * | 5/1930 | |
| CN | 105188490 | A | 12/2015 | |
| CN | 105085260 | | 4/2018 | |
| CN | 105085260 | B | 4/2018 | |
| CN | 109982573 | A | 7/2019 | |
| DE | 2429589 | | 1/1976 | |
| DE | 2429589 | A1 | 1/1976 | |
| EP | 115095 | * | 8/1984 | |
| EP | 3231297 | | 10/2017 | |
| EP | 3231297 | A1 | 10/2017 | |
| JP | 2019173590 | | 10/2019 | |
| JP | 2019173590 | A | 10/2019 | |
| KR | 101944648 | | 1/2019 | |
| KR | 101944648 | B1 | 1/2019 | |
| KR | 20200022896 | A * | 3/2020 | A23N 12/125 |
| WO | 2020065311 | | 4/2020 | |
| WO | 2020065311 | A1 | 4/2020 | |

OTHER PUBLICATIONS

R_roasting_RMCPhoto: Vacuum degassing a fresh roast_Feb. 23, 2019, p. 1-12. URL: https://www.reddit.com/r/roasting/comments/atttfp/vacuum_degassing_a_fresh_roast_ethiopia_sidamo/?rdt=56802 (Year: 2019).*

Quarta et al. [Furfurals removal from roasted coffee powder by vacuum treatment, 2011], Food Chemistry 130 (2012) p. 610-614. (Year: 2011).*

European Patent Office, Extended European Search Report, Application No. 21851523.7, Jul. 17, 2024, 11 pages.

Quarta, B., & Anese, M. (2012). Furfurals removal from roasted coffee powder by vacuum treatment. Food Chemistry, 130(3), 610-614, 5 pages.

Office Action dated Aug. 23, 2024, issued in Chinese Patent Application No. 202180065567.5, 30 pages.

Second Office Action dated Mar. 13, 2025, issued in corresponding Chinese Patent Application No. 202180065567.5, 8 pages.

Intellectual Property Office of Vietnam, Office Action, for corresponding Vietnam Patent Application No. 1-2023-01224, dated Feb. 28, 2025 [4 pgs.].

* cited by examiner

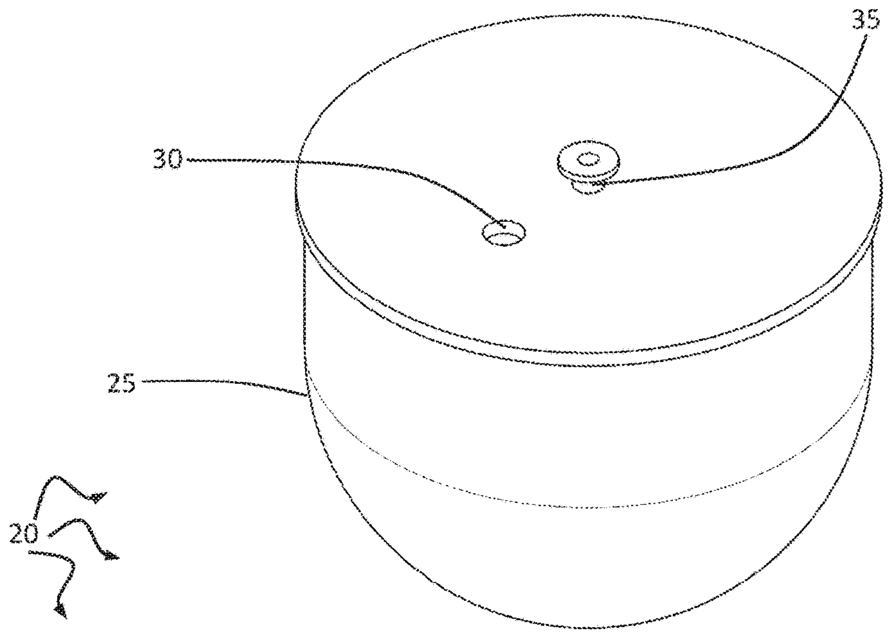
FIG. 1A
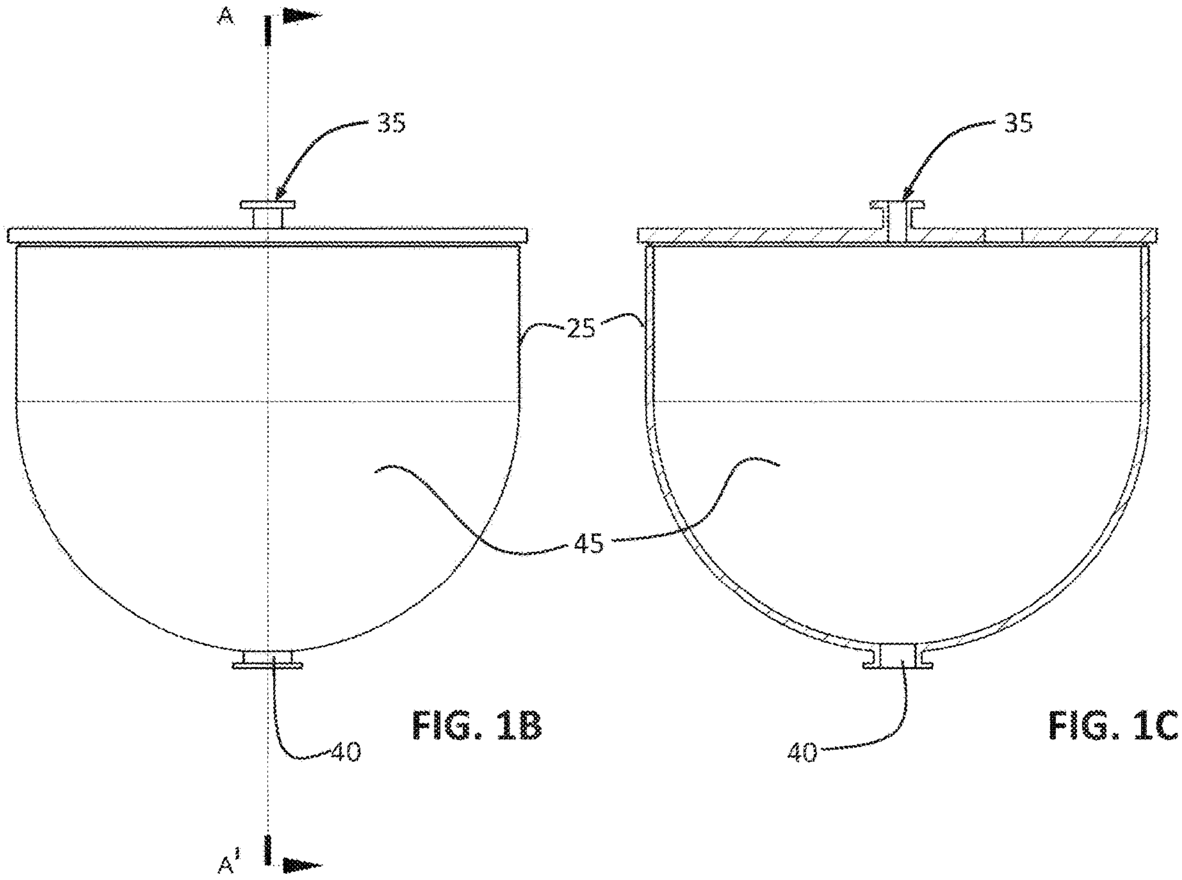
FIG. 1B
FIG. 1C
Section A-A'

SYSTEMS AND METHODS FOR REHABILITATING COFFEE BEANS AND BREWED COFFEE

CROSS-REFERENCE TO RELATED APPLICATIONS

This patent application claims priority to U.S. patent application Ser. No. 16/939,340, filed on Jul. 27, 2020, and also to U.S. Provisional patent application Ser. No. 63/093,045, filed on Oct. 16, 2020; 63/156,588, filed on Mar. 4, 2021; 63/156,517, filed on Mar. 4, 2021; and 63/209,487 filed on Jun. 11, 2021.

TECHNICAL FIELD

The invention disclosed herein relates generally to the field of coffee, and more particularly, to systems and methods for removing undesirable flavors from coffee beans and coffee solutions.

BACKGROUND

Coffee has been a treasured drink across much of the world for over 500 years. However, despite hundreds of years of experience in fermenting, roasting, and brewing coffee beverages, it remains difficult to consistently produce high-quality coffee beverages without a lingering, bitter and acidic aftertaste. Indeed, the quality of roasted coffee beverages run the gamut from the very rare and fine to the barely drinkable.

The art of roasting and brewing coffee beans over the last 50 years has evolved from a closely guarded secret to an established standard of perfection. Typically, raw coffee beans, often referred to as green beans, are placed into a rotating coffee convection roaster between 187° C. and 282° C. for 10 to 20 minutes, depending on the desired depth of roast. Roasting conditions are carefully controlled to develop flavors with a variety of notes, such as berry, citrus, chocolate, or floral, while attempting to preserve smoothness; however, these efforts are often at odds resulting in characteristically bitter or highly acidic products. Smoothness in coffee is very difficult to obtain, even with small batch roasting and fine bean quality.

Once the beans reach the desired temperature, they are quickly poured into a cooling table to rapidly quench the temperature while separating any remaining chaff from the beans. Once cooled to a sufficient temperature, the beans enter additional quality control steps such as metal detection, moisture verification, sizing, destoning and followed finally by bagging.

During the bagging process coffee beans are weighed and deposited into a wide variety of single layer or multi-layer package types, typically between 12 oz and 5 lbs in size, and often under the flow of an inert gas, such as nitrogen, to preserve freshness. In some cases, one-way valves may be placed in coffee bags to accommodate for beans continual release of byproduct gases produced during the roasting process (primarily water vapor and carbon dioxide).

Roasted coffee beans are made up of thousands of molecules ranging from low molecular weight acids to high molecular weight lipids and proteins. Flavor and aroma in coffee is produced during roasting from multiple thermally-activated mechanisms such as Maillard reactions, Strecker degradation, and breakdown of sulfur amino acids, hydroxy-amino acids, proline and hydroxyproline, trigonelline, quinic acid moieties, carotenoids, lipids, and the like. These complex reactions result in production of several classes of volatile molecules including sulfur compounds, pyrazines, pyridines, pyrroles, oxazoles, furans, aldehydes and ketones, acetates, phenols, alcohols, and organic acids, in addition to nonvolatile molecules, such as caffeine. In addition to desirable flavors and aromas, the roasting process is known to result in the formation of several undesirable acids including formic acid, acetic acid, lactic acid, chlorogenic acid, caffeic acid, and the like, many of which form due to the thermal degradation and oxidation of carbohydrates, such as sucrose. Coffee roasters presently must compromise between the development of desirable flavor molecules, such as 2-furanmethanol or 3-methylbutanal, and undesirable flavor molecules, such as acetic acid, formic acid, or isovaleric acid.

Additional measures to reduce the characteristic bitterness or acidic notes in coffee occur at the brewing stage of coffee making. Careful control of brewing temperatures and times are used to extract flavor while minimizing harsh, bitter notes caused by overextraction due to long brew cycles or scalding due to excessive water temperatures. Cold brewing is a slow, low temperature extraction process designed to increase the brew concentration while minimizing harsh flavors. Even with cold brew techniques, harsh flavors in coffee beverages persist.

Other coffee bean process techniques may also contribute to adverse flavor creation before or after coffee bean roasting. Decaffeination as an example, most often uses solvent extraction to selectively remove caffeine from unroasted coffee beans. The most common technique is to use ethyl acetate as a polar aprotic solvent to permeate the bulk cellular structure and selectively dissolve caffeine.

Beverage quality may vary greatly from manufacturer to manufacture, as well as from batch to batch produced by a given manufacturer. This arises in part because of inconsistent processing and in part due to variations in the source and quality of raw materials. One source of variance in beverage quality is the presence of unwanted roasting byproducts in the beverage generated as side effects during roasting and flavor development and contribute to adverse flavors in coffee beverages.

While countless methods to adjust roasting times and temperatures to improve coffee flavor profiles and smoothness while simultaneously reducing harsh and bitter notes in coffee beverages have been attempted, present products still represent a compromise desirable flavor development and harsh flavor creation. Thus, there remains a need for means to remove unwanted harsh and bitter flavors in coffee beans and beverages while leaving desirable aromas and flavors. The present novel technology addresses this need.

BRIEF DESCRIPTION OF THE DRAWINGS

FIG. 1A is a perspective view of a coffee rehabilitation system according to a first embodiment of the present invention.

FIG. 1B is a side elevation view of the system of FIG. 1A.

FIG. 1C is a cutaway view of the system of FIG. 1B along line A-A'.

DETAILED DESCRIPTION

Figure 1D:
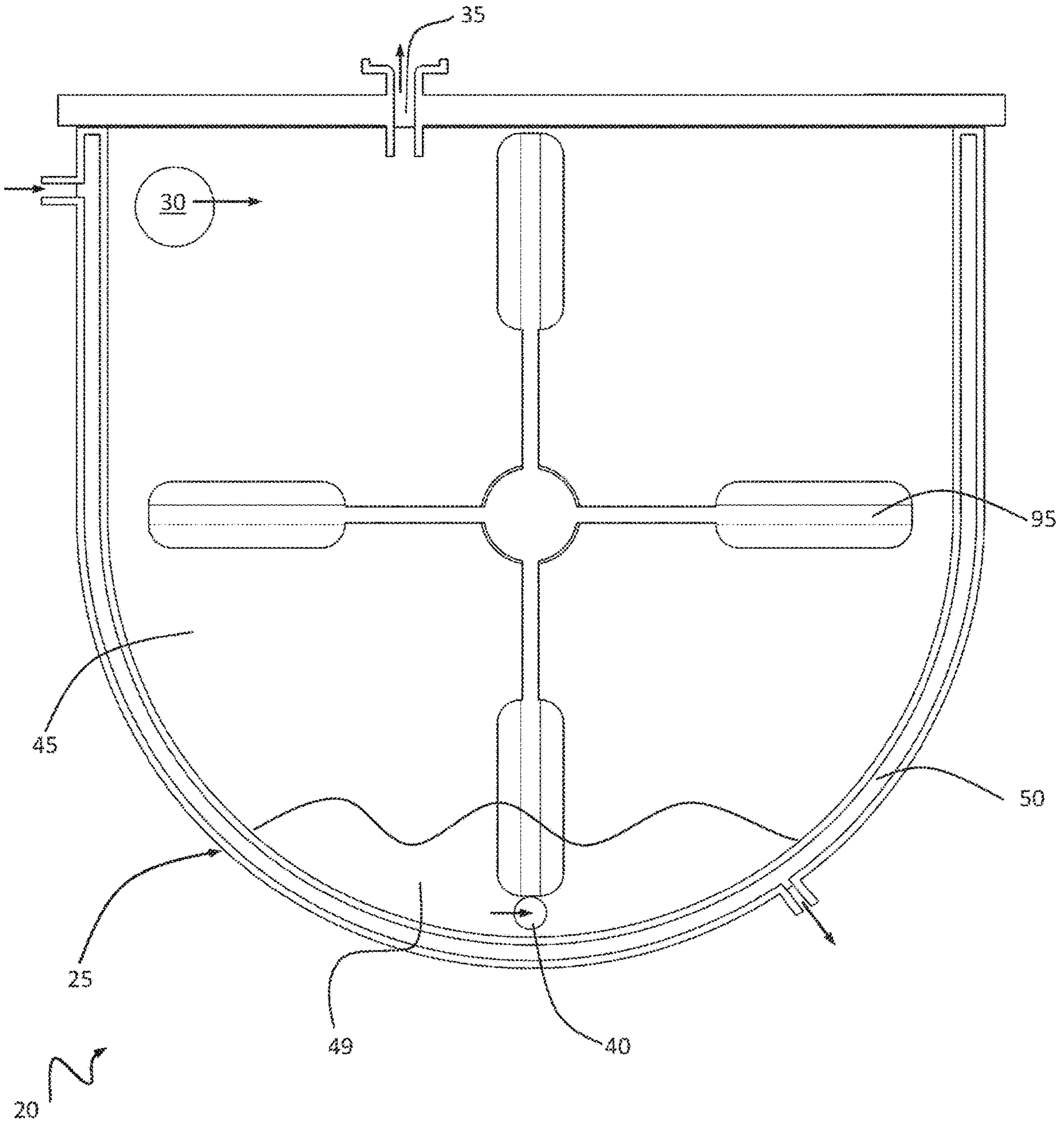
FIG. 1D is a cutaway view of the system of FIG. 1A showing internally mounted agitators.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Aspects of the disclosure relate to methods of removing unwanted congeners from coffee compositions and to coffee compositions (e.g., beverage compositions) comprising reduced levels of unwanted congeners. As used herein, "coffee composition" refers to a composition comprising coffee. For example, a coffee composition may comprise coffee beans, ground coffee beans, or a coffee solution. As used herein, "removing" a congener from a coffee composition means reducing the quantity of that congener in the coffee composition. As used herein, where a congener is "removed" from a coffee composition, it is to be understood that the quantity of the congener may be reduced partly, substantially, or entirely or effectively entirely (i.e., to the point that it is not detectable by one or more analytical techniques) relative to the amount of congener present in the coffee composition before the congener was removed. In some embodiments, after a congener is "removed" from a coffee composition, the congener remains detectable in the coffee composition by one or more analytical techniques. In some embodiments, after a congener is "removed" from a coffee composition, the congener is not detectable in the coffee composition by one or more analytical techniques.

Removal of some or all of the unwanted congeners in a coffee composition may be desired because the unwanted congener(s) are inherently toxic or because the unwanted congener(s) (in their present concentration(s)) contribute an unpleasant or negative organoleptic experience. One congener found in coffee compositions is ethyl acetate (also referred to herein as "EA"). Ethyl acetate is an ester molecule formed through the esterification of ethanol (alcohol) and acetic acid (vinegar). Ethyl acetate is also a polar, aprotic solvent with amphipathic properties, and is commonly used in decaffeination of raw coffee beans. As a result, consumers are highly sensitive to small changes in ethyl acetate concentration both in the olfactory reception, which may cause a rough peak and sharp bite in the finish, and in the cellular equilibrium which may cause a solvent-like burn on the rear of the oral cavity. In fact, it is the ethyl acetate concentration that controls the perceived "bite" characteristic in the peak and finish of fermented foods and beverages. Since ethyl acetate also serves as a polar-aprotic solvent during consumption, it may aid in the detection of other flavor molecules. As a result, an ethyl acetate concentration too low may inhibit a consumer's ability to detect other desirable flavors and aromas.

Proper balancing of ethyl acetate concentrations at the parts-per-million, or even parts per billion, levels is necessary to optimize the organoleptic properties of foods and beverages. For example, ethyl acetate in very low quantities operates on certain combinations of specialized G protein-coupled olfactory receptors to yield a pleasant or enhanced organoleptic experience, while at greater concentrations ethyl acetate operates on those same receptors to generate an unpleasant or negative organoleptic experience. Such a negative organoleptic experience may be characterized by a bite, throat burn, bitterness, a metallic taste, a lingering aftertaste, head recoil, involuntary shudder, triggering of the gag reflex, and combinations thereof. Reduction or removal of ethyl acetate may eliminate these negative organoleptic experiences, and reduction of ethyl acetate concentration to certain levels may actually enhance the already desirable organoleptic properties of the coffee.

In some embodiments, the methods disclosed herein are applied to produce a purified coffee composition, defined herein as a coffee composition from which a quantity of one or more unwanted congeners has been removed. For example, in some embodiments, the methods disclosed herein are applied to reduce the ethyl acetate concentration of a coffee composition to by 10% to 97% of initial unprocessed concentrations, as measured in the liquid phase of the coffee composition as measured by gas chromatography mass spectrometry.

In some embodiments, the purified coffee composition is an organoleptically improved beverage comprising coffee that has been prepared from a starting coffee bean composition. That is, in some embodiments, the methods disclosed herein are applied to produce an organoleptically improved beverage from a starting coffee composition, wherein the organoleptically improved beverage comprises coffee. In some embodiments, the methods disclosed herein are applied to produce an organoleptically improved beverage from a starting coffee composition, wherein the organoleptically improved beverage comprises dissolved coffee beans and wherein the starting coffee bean composition from which the beverage was derived possesses one or more undesirable organoleptic properties not found in the organoleptically improved beverage. In some embodiments, said one or more undesirable organoleptic properties are selected from the group consisting of harsh finish, sharp finish, biting finish, solvent finish, astringent finish, heavy finish, muted flavor, a solvent overtone in the peak and/or the finish, dry taste on the palate, a harsh peak that overshadows one or more flavors (e.g., one or more delicate flavors), bite, throat burn, bitterness, metallic taste, lingering aftertaste, cause of head motion, e.g., head recoil, head-shaking, head-tilting, or head-tensing, cause of involuntary physiological response, e.g., shudder, cause of gag reflex, and combinations thereof. In some embodiments, the methods disclosed herein are applied to produce an organoleptically improved beverage from a starting coffee composition, wherein the organoleptically improved beverage comprises dissolved coffee beans. In some embodiments, the methods disclosed herein are applied to produce an organoleptically improved beverage from a starting coffee composition, wherein the organoleptically improved beverage comprises a coffee solution and wherein one or more desirable organoleptic properties of the beverage are at least substantially similar to at least one corresponding desirable organoleptic property of the coffee-containing composition from which the beverage was derived. In some embodiments, the methods disclosed herein are applied to produce an organoleptically improved beverage from a starting coffee composition, wherein the organoleptically improved beverage comprises a coffee solution and wherein one or more desirable organoleptic properties of the beverage are substantially improved over the corresponding one or more corresponding desirable organoleptic properties of the coffee composition from which the beverage was derived. In some embodiments, said one or more desirable organoleptic properties are selected from the group consisting of smooth finish, rich finish, balanced finish, bright peak, flavorful peak, balanced peak, balanced peak that accentuates nuances of flavor, and combinations thereof.

Consumers often describe the transient experience of flavor in three unique phases including the 'start,' 'peak,' and 'finish,' which follow the corresponding sensory mechanisms of taste, smell, and a residual detection and molecular degradation. Each phase is dominated by specific sensory sources, and an over- or under-expression of flavor and aroma during each phase may determine the overall desirability of the food. Consumers initially begin with taste of the food or beverage on the tongue where they may experience a combination of tasting notes that may include sweet, sour, bitter, savory, fatty, and salty. Tasting notes are detected by multiple types and variants of receptors (commonly referred to as taste buds) primarily found on the tongue. While some tasting notes are governed by a single receptor type, other tasting notes, such as bitterness, may be perceived through a combined signal of more than twenty-five receptor variants. An over- or under-expression of any one of the receptors may cause alarm to the consumer and thereby decrease the food's perceived positive organoleptic properties. As a result, consumers often refer to organoleptically desirable foods or beverages as 'balanced.'

During consumption, taste may almost immediately be followed by smell, often described as the peak, as volatile aromas travel back down the throat and up into the olfactory cavity. The additional time needed for volatile compounds to travel from the oral cavity to the olfactory cavity creates the perceived time lag between the start and peak of a consumer experience. Smell is transmitted primarily through G-protein coupled olfactory receptors, with nearly one thousand different olfactory receptors responsible for smell, each which is highly sensitive to a particular molecule. Olfactory receptors are particularly selective to esters, such as ethyl acetate, a certain class of organic molecule that consumers often refer to as 'essences.' The senses of taste and smell differ in their sensitivities. For comparison, tastes may typically discern concentration changes in parts-per-hundred, while smell may discern changes in concentration of as little as parts-per-billion. As with taste, the organoleptic properties of a food or beverage may be determined by the balance of smell experienced through a combination of receptors. An over- or under-expression of any one receptor may cause the perceived balance of a food or beverage to decrease, resulting in a less desirable product.

The finish in foods and beverages is more complicated than the start or the peak. During the finish molecules in the oral cavity begin to degrade through various mechanisms, such as hydrolysis and catalysis, volatile compounds promoted through the heat and convection in the oral cavity continue to evaporate from the oral cavity and travel to the olfactory cavity, and the cellular equilibrium of the oral cavity itself begins to alter as a result of the food or beverage. Foods or beverages that drastically alter the oral cavity during consumption often have a finish described as ‘sharp,’ hot; or ‘biting’ (examples include hot sauce, shelf-stable condiments, or spirits). In low concentrations, these undesirable experiences may be described as ‘rough,’ ‘heavy,’ astringent, full of tannins, or the like. On the other hand, foods and beverages that maintain the taste, smell, and cellular equilibrium as they dilute on the palate are often referred to as having a ‘fresh,’ ‘savory,’ ‘crisp,’ ‘smooth,’ ‘delicate,’ or ‘refined’ finish, and are typically considered more desirable.

The vapor pressure and perceived concentration of ethyl acetate does not directly correspond to the molecular concentration due to the complex intermolecular interactions in a given food or beverage. Thus, balance may not simply be controlled through measurement and titration. A properly balanced food or beverage may instead create a condition in which an ethyl acetate equilibrium (also referred to herein as an “EAE”) may be perturbed and re-established under a different concentration. The present technology achieves this goal (perturbing an ethyl acetate equilibrium of a coffee composition and re-establishing it under a different concentration) without altering the concentration of other desirable molecules (e.g., ethanol) through the use of food or beverages’ complex steric hindrance. In this way, the bite or roughness typically experienced by consumers from ethyl acetate and other fermentation byproducts present in an initial coffee composition may, through methods disclosed herein, be rebalanced to a more organoleptically favorable condition in a resulting organoleptically improved beverage. Through this process, smells in the peak of a consumer experience will often be perceived as brighter and more defined since they are not competing with ethyl acetate, and the finish will often be perceived as ‘smoother’ and more ‘refined,’ thereby creating more desirable organoleptic properties in the resulting organoleptically improved beverage.

Along these lines, a further aspect of the disclosure relates to methods of measuring vapor phase ethyl acetate concentration in coffee compositions and the use of said methods to optimize the organoleptic properties of coffee compositions. Conventional methods of measuring congener concentration (e.g., ethyl acetate concentration) in beverage compositions such as coffee, wine, beer, spirits, as well as fermentation byproducts, such as natural or distilled vinegar utilize direct infrared, HPLC, and/or gas chromatography mass spectrometry measurement of the liquid phase of the sample. Conventional wisdom is if the chemical makeup is the same, or at least very similar, then the flavor should be the same, or at least very similar. While these methods are very good at measuring absolute congener concentrations in a beverage, they have been found to correlate to flavor only loosely and have not been found to be consistent enough to predict the organoleptic properties of coffee compositions. Without wishing to be bound by theory, it is believed that one reason for the lack of correlation and/or consistency is that the consumer experience of flavor is the result of complex intermolecular interactions with multiple sensor phases. While taste sensors on the tongue are important in determining the basic flavor of a beverage, most of the nuances of flavor and aromatic complexities are experienced through the olfactory. The utilization of these precise instruments to fingerprint the consumer flavor experience has often been found to be inaccurate.

Aspects of the present disclosure address those issues. In some embodiments, the olfactory experience of a beverage may correctly be correlated by measuring the partial pressure of volatile molecular components sampled from the atmosphere in fluidic communication with a liquid phase and/or solid phase sample of the beverage that has reached equilibrium saturation under closed system conditions. The atmospheric phase equilibrium may be established with air and/or inert gas phase environments under ambient pressures and temperatures. In some embodiments, the temperature of the sample and/or the atmosphere may be adjusted to match the preferred consumption conditions of the beverage. In the present method, complex intermolecular interactions in the liquid and/or solid phase of the sample beverage may be controlled for by establishing a quasi-equilibrium condition with a vapor phase. While the liquid phase concentration of molecular constituents, such as ethyl acetate, may shift from beverage to beverage, the atmospheric phase concentration may remain relatively consistent and therefore represent a more accurate representation of the olfactory experience and, therefore, of the organoleptic properties of a beverage.

In an embodiment of the disclosed method, a 1 mL to 5 mL liquid sample, or 0.5 to 5 grams of solid coffee beans, is placed in a vial having a total volume of 0.5 to 5 times the sample volume, which is then sealed with a separate cap to form an isolated atmosphere. The sealed sample may be allowed to rest undisturbed, or may alternatively be agitated, such as for a period of from 5 seconds to 5 minutes or until an equilibrium condition is established between the atmospheric phase and the sample. A portion of known volume of the vapor phase is be removed from the vessel, analyzed using gas chromatography mass spectrometry, and examined for specific concentrations of molecules in the vapor phase. Alternatively, or in addition, the portion of known volume of the vapor phase is analyzed using one or more chemically selective sensors that are placed in fluidic communication with a sample of the equilibrium atmosphere. For real-time analysis, a chemically selective sensor may be placed in direct atmospheric communication with the isolated environment and partial pressure concentrations of select molecules may be detected through correlative and calibrated signals. In some embodiments, the chemically selective sensor may be specific for detection and measurement of ethyl acetate. When such an ethyl acetate-specific sensor is employed, a real time analysis of the organoleptic properties, particularly the smoothness of a coffee beverage, may be predicted by measuring the ethyl acetate partial pressure of a gas phase equilibrium above the sample beverage.

As shown in FIGS. 1A-20, the present novel technology relates to an apparatus 20 for preferentially removing quantities of one or more predetermined unwanted congeners from coffee, as coffee beans (green and/or roasted) and/or coffee extract solutions and/or processed coffee powders, also referred to herein as coffee solutions and/or coffee beverages, such as cold brew coffee, percolated or drip coffee, espresso coffee, and like beverages. In one embodiment, the apparatus 20 includes a pressure vessel 25 having an inlet port 30, a vapor outlet port 35, and an outlet port 40, all in fluidic communication with an internal pressure controllable chamber 45 defined by the pressure vessel 20. Inlet port 30 and outlet port 40 may be liquid ports in the cases of coffee beverages, or solid product ports, in the case of coffee beans or coffee grounds. While the system 20 may be used to treat coffee in liquid (extract) form and/or solid (bean) form, with ports 30, 40 configured for use with solids, liquids, or both, the following example focusses on the treatment of liquid coffee extract for simplicity.

The pressure vessel 25 may include a water jacket 50 or like temperature controller at least partially enveloping the pressure chamber 45 and in thermal communication with the same. Liquid inlet port 30 is typically connected in fluidic communication, such as via a pipe 55, with a liquid pump 60. Pump 60 is connected in fluidic communication with coffee source 65. Typically, at least one valve 70 is operationally connected in line between coffee source 65 and liquid inlet port 30. The valve 70 may be connected between inlet port 30 and pump 60, between pump 60 and coffee source 65, or valves 70 may be connected in both positions.

While bulk vacuum storage has been developed for whole bean and ground coffee storage to minimize lipid oxidation and improve shelf life for extended periods of time, vacuum storage is known to cause significant loss of moisture, flavor, and aroma resulting in product quality degradation. As a result, vacuum storage is typically reserved for low quality and low price, pre-ground coffee where product degradation is not an important factor in consumer behavior.

Vapor outlet port 35 is typically connected in fluidic communication with a vacuum pump 75, which is connected in fluidic communication with a collection vessel 80. Vacuum pump 75 typically operates to remove and direct evolved vapor from the pressure vessel 25 for collection in the collection vessel 80 at a desired pressure, as well as establish a partial vacuum within the pressure controllable chamber 45. The collection vessel 80 may be a cold trap, a pressure-controlled vessel, or the like. Typically, at least one valve 70 is operationally connected in line between collection vessel 80 and vapor outlet port 35. The valve 70 may be connected between vessel 45 and pump 75, between pump 75 and outlet port 35, or valves 70 may be connected in both positions. Collection vessel 80 may be emptied and the accrued distillate recovered.

Liquid outlet port 40 is typically connected in fluidic communication with pump 85, which is connected in fluidic communication with coffee collection vessel 90. Typically, at least one valve 70 is operationally connected in line between coffee collection vessel 90 and liquid outlet port 40. The valve 70 may be connected between vessel 45 and pump 85, between pump 85 and collection vessel 90, or valves 70 may be connected in both positions.

Example 1

As illustrated generally in FIGS. 1A-1E, the above-described assembly 20 may be embodied to treat coffee beans or coffee beverages on a batch-by-batch basis. Pressure vessel 25 includes ports 30, 35, 40 as described above, as well as water jacket 50 or like temperature control mechanism encapsulating pressure chamber 45 in thermal communication therewith. Agitator 95 is positioned within pressure chamber 45 to facilitate stirring/vibration/bubbling of a volume of coffee beverage contained therein. A partial vacuum in pressure chamber 45 may be established via energization of vacuum pump 75.

Figure 1E:
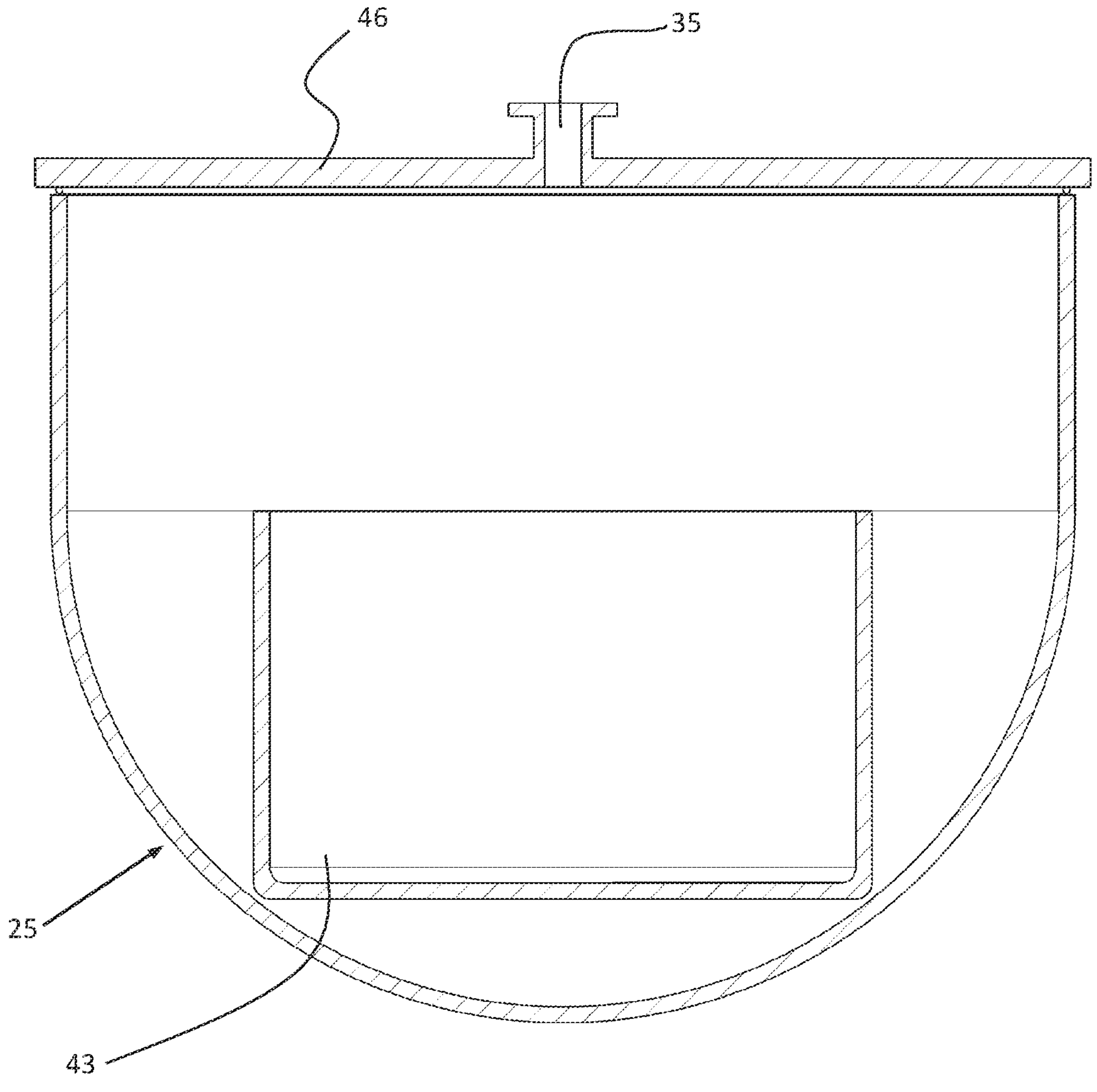
FIG. 1E is a cutaway section view of the coffee rehabilitation system of FIG. 1A with a secondary open container positioned therein.

In FIG. 1E, a coffee solution contained in an open container 43 is placed in the pressure chamber 45. A vacuum lid 46 is then engaged with the vacuum chamber 45, thereby isolating the vacuum chamber environment from the surrounding exterior environment, and the pressure in the vacuum chamber 45 is decreased by energization of a vacuum pump 75 in operational communication with the vapor outlet port 35. Once the vacuum chamber pressure reaches a specified level, the vacuum chamber pressure is then increased to atmospheric pressure and the lid 46 is removed, followed by the container 46 containing the now vacuum-treated coffee solution.

Example 2

Figure 2:
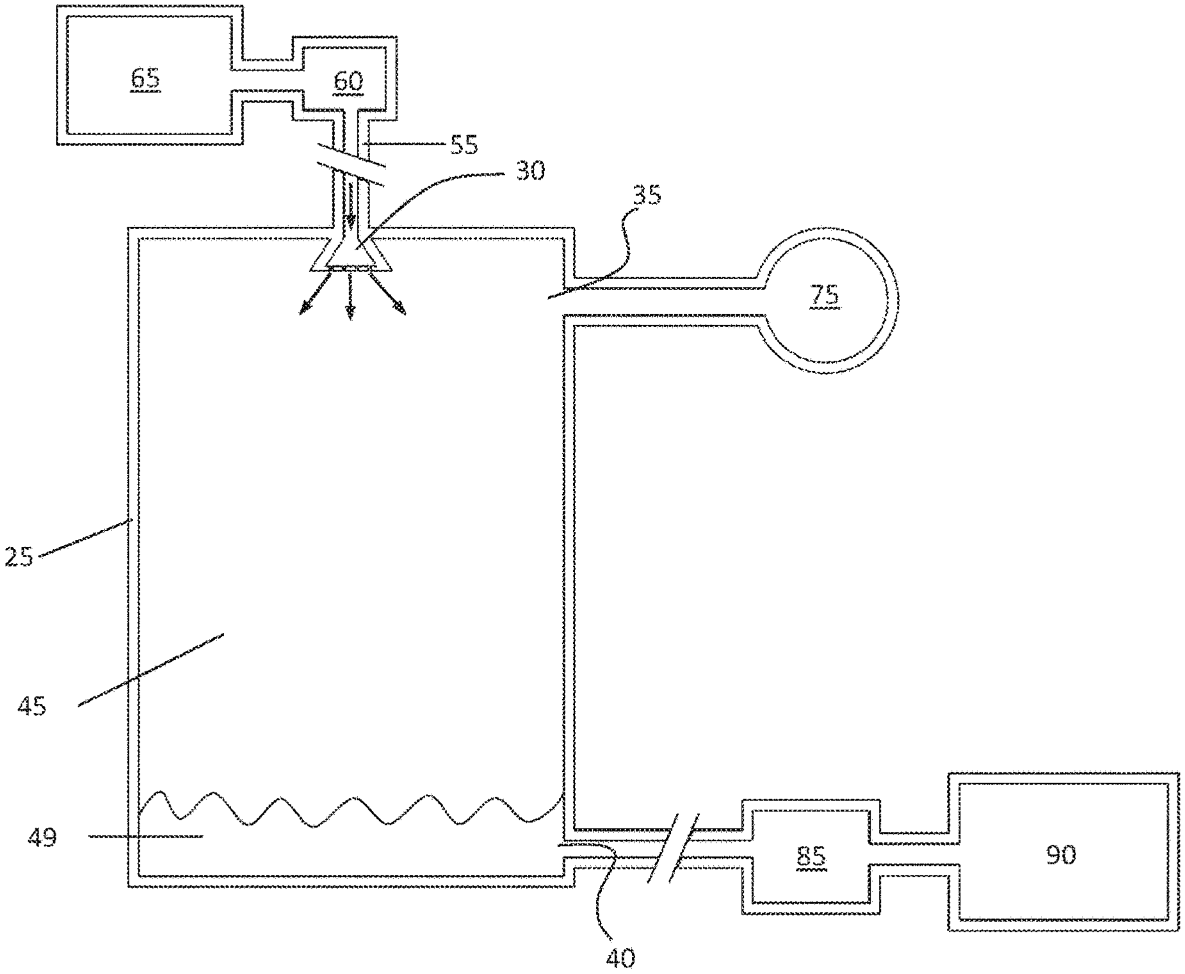
FIG. 2 is a cutaway section view of a coffee rehabilitation system according to a second embodiment of the present invention.

As illustrated in FIG. 2, the above-described assembly 20 may take an embodiment to treat coffee beans or coffee solutions as a continuous flow process. Liquid inlet port 30 is configured as a spray head and is positioned to spray coffee solution pumped from source tank 65 into the pressure chamber 45 already pumped down to the desired partial vacuum pressure. The spray of coffee solution travels through the pressure chamber 45 to collect or pool at the bottom of the pressure vessel 25, where it may be pumped out through outlet port 40. In some embodiments, inlet port 30 is configured as a nozzle, while in other embodiments a separate nozzle is operationally connected to inlet port 30 to accelerate and direct the incoming liquid.

Example 3

Figure 3:
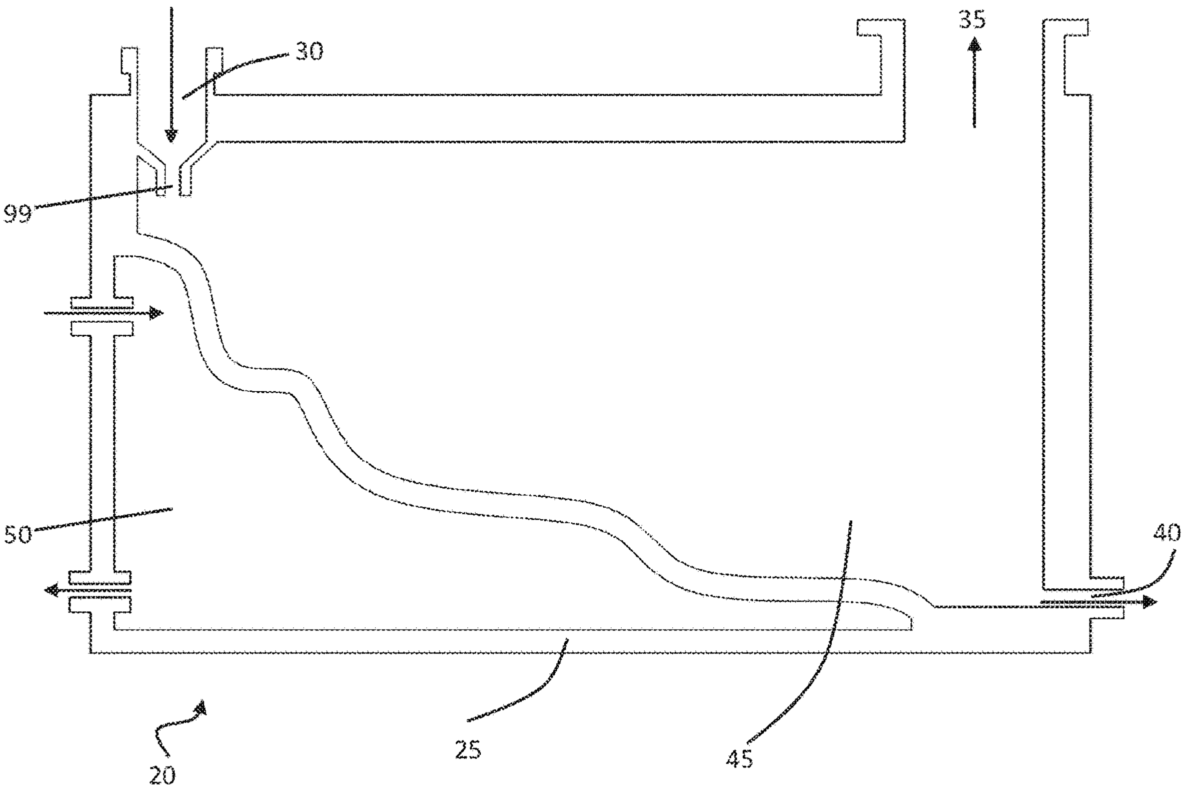
FIG. 3 is a cutaway section view of a coffee rehabilitation system according to a third embodiment of the present invention.
Figure 4A:
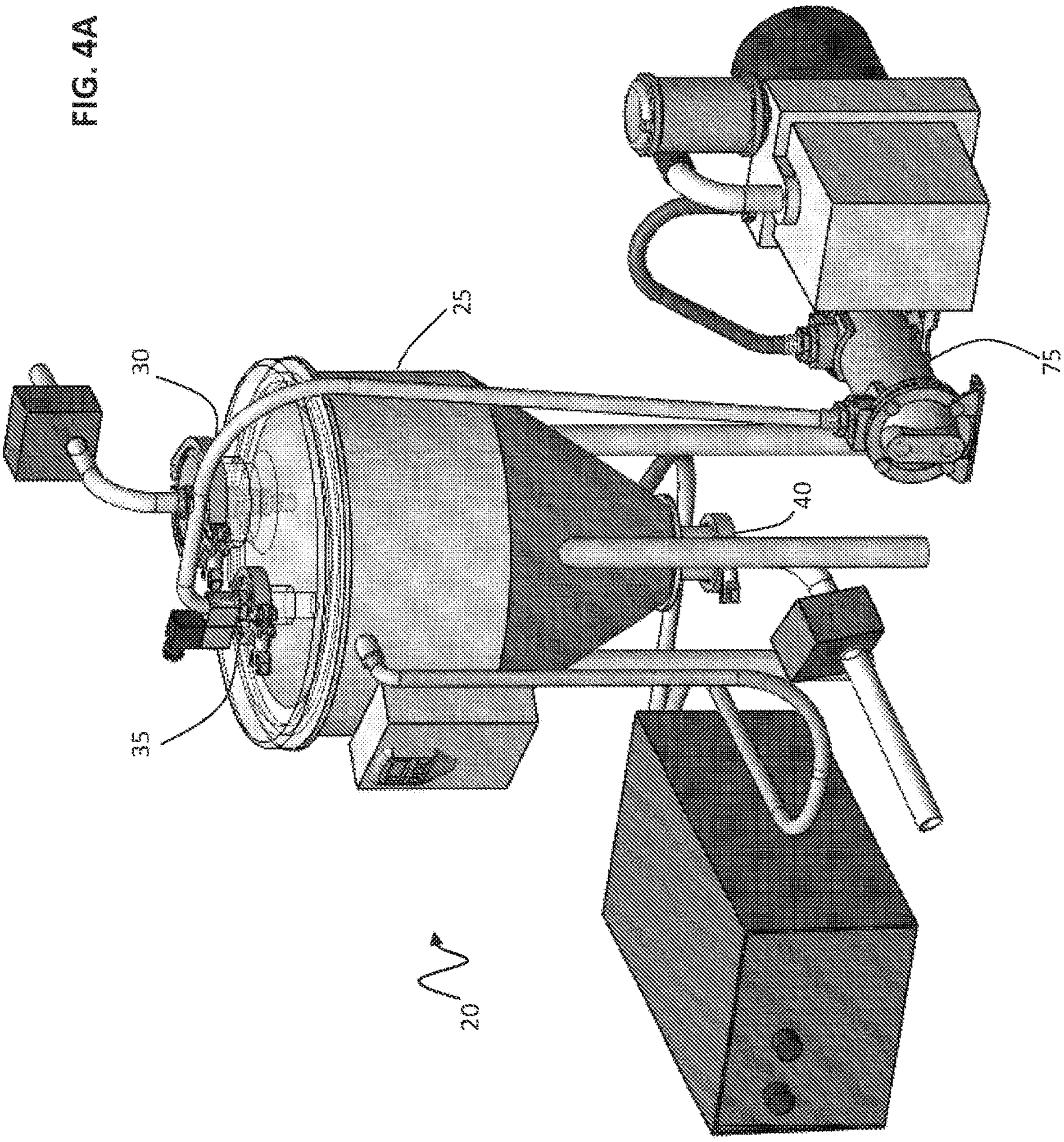
FIG. 4A is first perspective view of a coffee rehabilitation system according to fourth embodiment of the present invention.
Figure 4B:
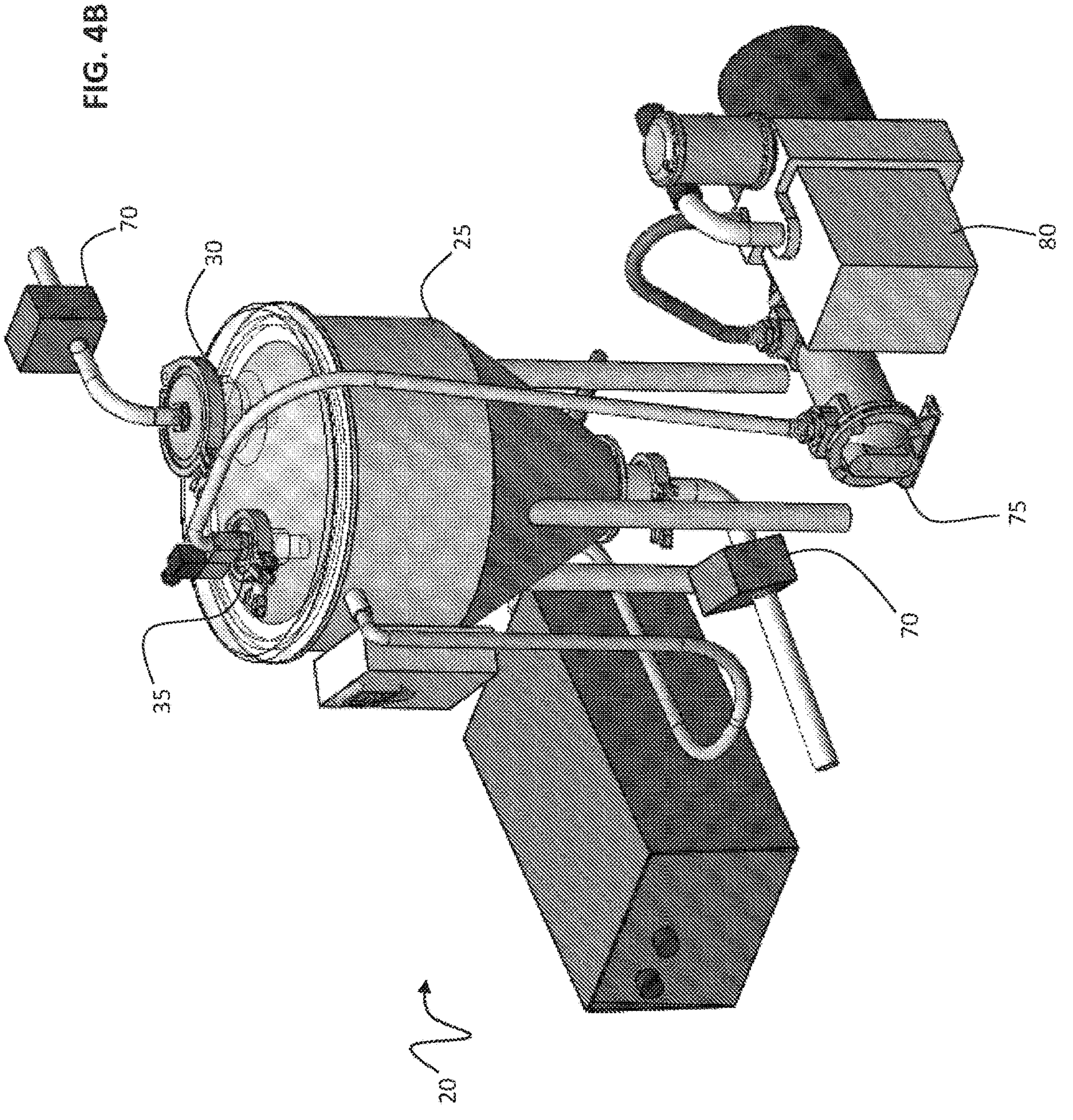
FIG. 4B is a second perspective view of the coffee rehabilitation system of FIG. 4A.
Figure 4C:
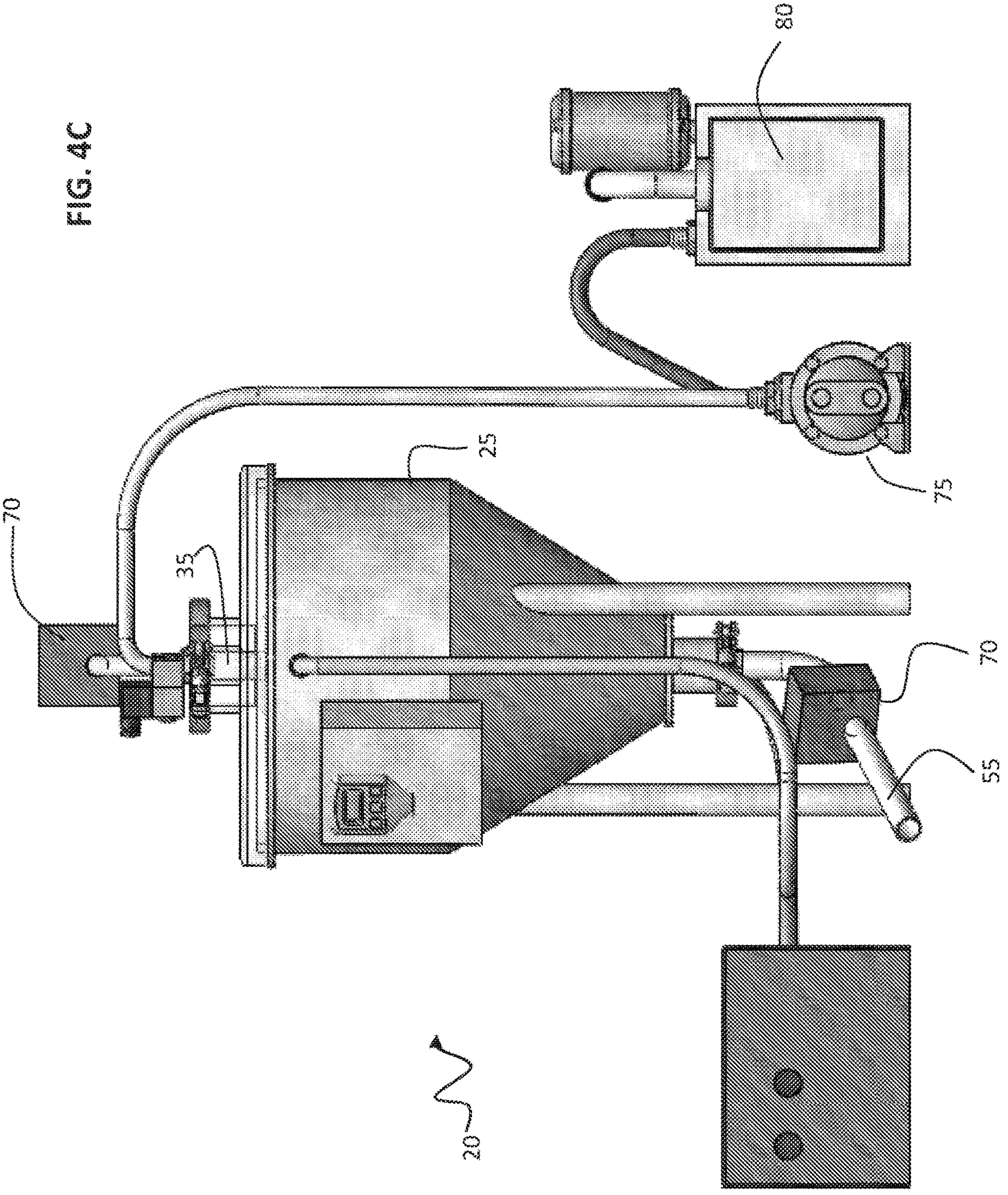
FIG. 4C is a front view of the coffee rehabilitation system of FIG. 4A.
Figure 4D:
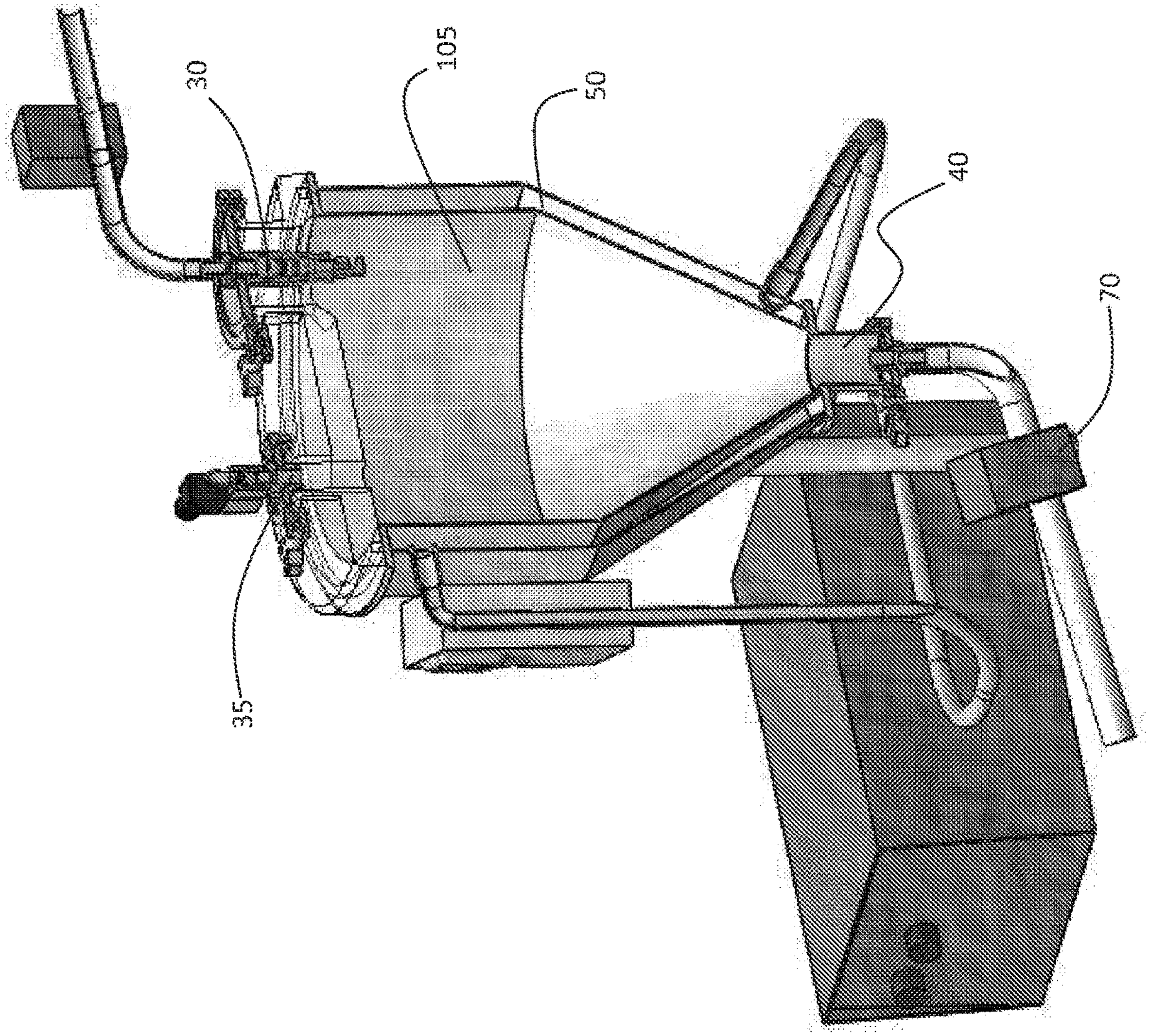
FIG. 4D is a first cutaway view of the coffee rehabilitation system of FIG. 4A having a smooth interior wall.
Figure 4E:
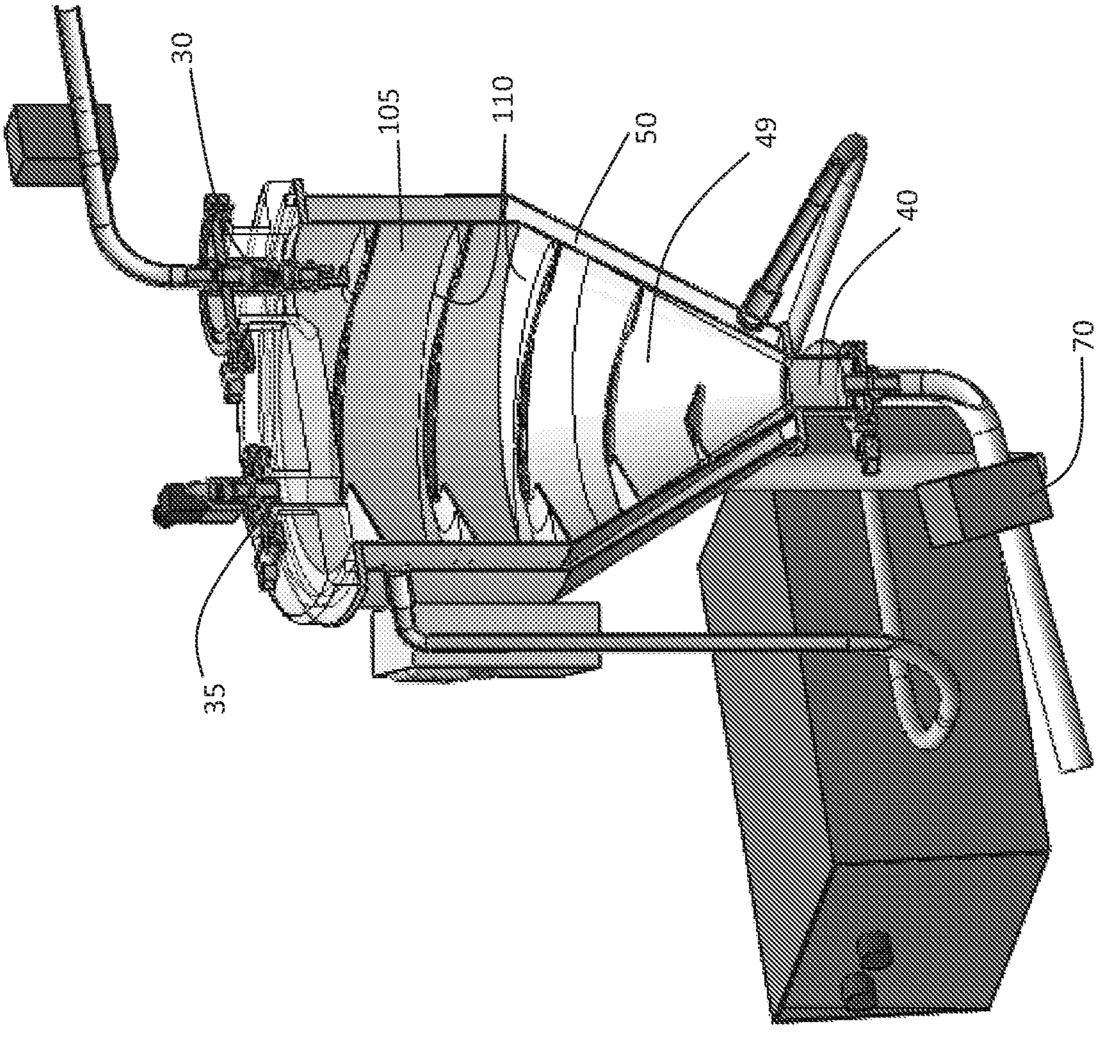
FIG. 4E is a second cutaway view of the coffee rehabilitation system of FIG. 4A having a raced interior wall.
Figure 4F:
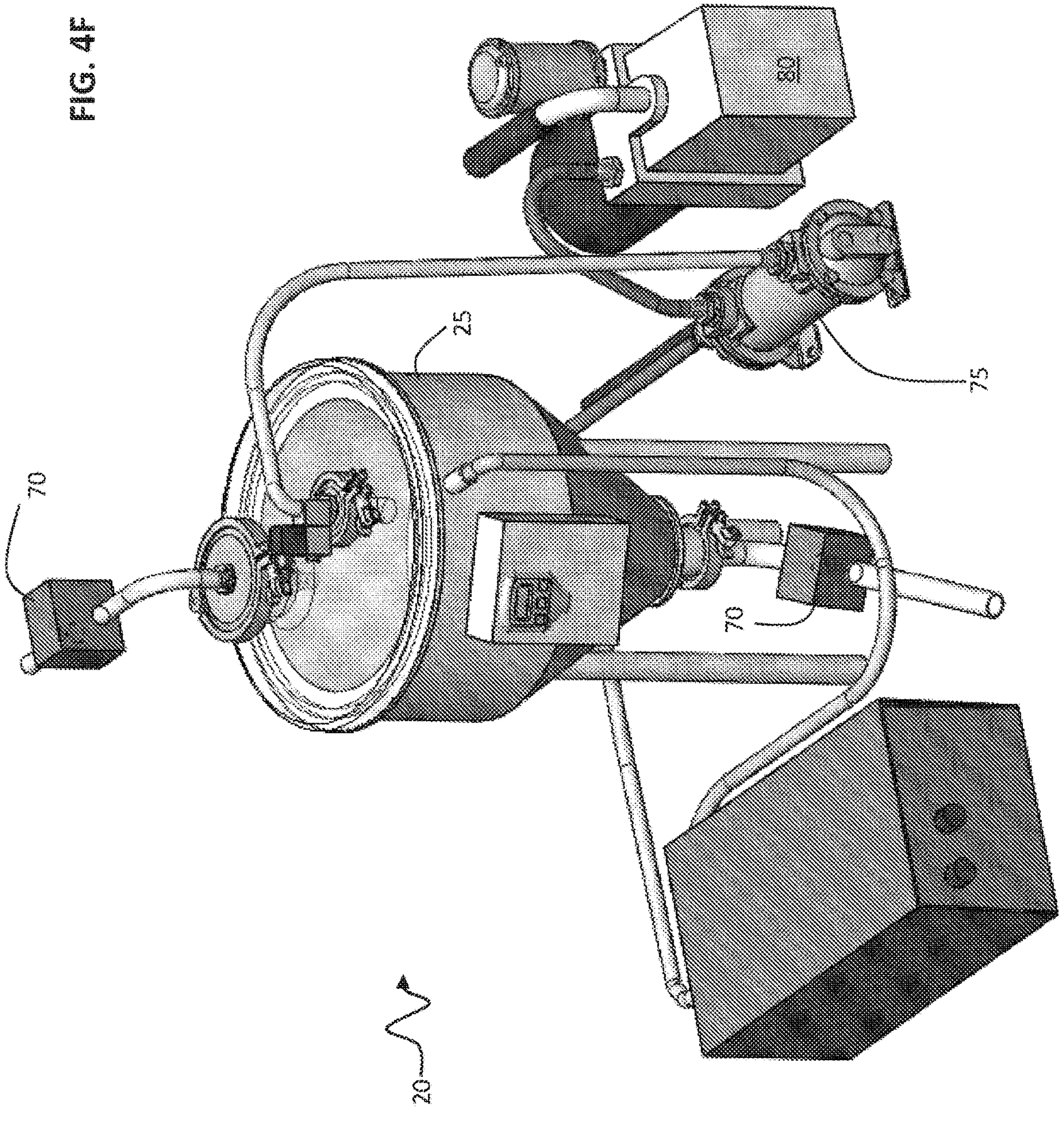
FIG. 4F is a third perspective view of the coffee rehabilitation system of FIG. 4A.

As illustrated in FIG. 3, the above described assembly 20 may take another embodiment to treat coffee solution solutions as a continuous flow process. The liquid inlet port 30 may empty onto one end of a ramp 100 where coffee solution pumped from source tank 65 spreads into a thin layer or sheet and flows downhill to pool at the other end of the ramp 100. Congeners may be evolved from the flowing coffee solution sheet into the partial vacuum environment inside the pressure chamber when the vacuum pump 75 is energized. The treated coffee solution may be pumped out of pressure chamber 45 and into collection vessel 90.

Example 4

As illustrated in FIGS. 4A-4E, the above-described assembly 20 may take still another embodiment to treat coffee solution as a continuous flow process. Vessel 25 is typically acorn-shaped, with a circular top to bottom cross-section that decreases in diameter from top to bottom (in this example, the top-down sectional profile has a cylindrical portion atop a conical portion), and a chevron-shaped side sectional profile (in this example, the side sectional profile has a rectangular upper portion and a triangular lower portion). Vessel typically includes a water jacket exterior 50 encasing a pressure controllable chamber interior 45. Liquid inlet port 30 positioned near the top of the vessel 25 injects coffee solution pumped from tank 65 into pressure chamber 45 wherein injected coffee solution is under sufficient pressure upon injection to be moving quickly enough to follow a spiral path along the inside of the pressure chamber 45 and ultimately pool at the bottom. Typically, the coffee solution defines a thin stream or ribbon that circles the vessel 25 a plurality of times while the partial vacuum therein (as provided by the energized vacuum pump 75 connected in fluidic communication therewith) evolves unwanted congeners therefrom to yield a treated and purified coffee solution. The purified coffee solution pools at the bottom of the pressure chamber 45 and may be pumped therefrom via liquid pump 85 into collection vessel 90. In some embodiments, the inside wall 105 of pressure chamber 45 is grooved or contoured no to help guide flowing coffee solution in a helical path from inlet port 30 to outlet port 40. Typically, the inside wall 105 would include a helical groove or race 110 to guide inlet liquid from the inlet port 30 around the inner wall several times to the outlet port 40.

In other like embodiments, vessel 25 may have convex or concave (see FIG. 5A) interior sectional contours. A concave shape profile may enable slow post inlet port liquid flow, followed by a deep cavity or reservoir formed near the outlet port 40 for sump modulation.

Ports 30, 35, and 40 of a first pressure chamber 45 may be in connected fluidic communication with other ports 30, 35, and 40 of other similar or identical pressure chambers 45 such that a plurality of pressure chambers 45 may be run in parallel from central vacuum 75 and fluidic pumps 60, 85. In this embodiment, fluid may be regulated individually or at fluidic manifolds connected in liquid communication with each respective pressure chamber 45. Chamber 45 typically has a processing volume of 0.025 liters/minute to 0.6 liters/minute throughput per liter of processing chamber volume for coffee solution and/or 0.043 to 0.38 kilograms of beans per liter of processing chamber volume for beans.

In some embodiments, a floater valve 91 may be used to prevent dry sump of the liquid outlet port 30 and regulate a minimum sump level. Under operation a floating valve 91 may open the liquid outlet port 40 once sufficient liquid enters the chamber 45. In the case where the liquid outlet pump 85 removes liquid sufficiently fast to decrease the liquid below float level, the floater valve 91 may form a pressure gradient between the vessel 45 and liquid outlet pump 85 preventing further liquid removal. One added benefit of a floater valve 91 is to prevent vessel atmosphere from being pressurized back into the cleaned or treated liquid leaving the liquid outlet port 40.

Sensors 93 may also be used to provide feedback to regulator valves 94 to maintain a positive volume above liquid outlet port 40 and prevent depressurization of vessel atmosphere in the process fluid. Sensors 93 may be in direct communication with the vessel sump liquid (typically vacuum-treated coffee solution solution), such as in the case of optical, inductive, or acoustic sensors 93, or indirectly monitor the fluid level with an acoustic, ultrasonic, or thermal sensors 93 around the fluid outlet port 40.

Liquid pumps 60, 85 as described herein may be variable displacement pumps, in the case of diaphragm pumps or piston pumps, or may be fixed displacement pumps, in the case of turbine pumps. Fluidic pumps 75, 85 in communication with the outlet ports 35, 40 may experience thirteen to fifteen PSI of negative pressure and may need to be combined in series to provide sufficient suction; as used herein, 'vacuum pump' may mean a single pump unit or a plurality of pump unites operationally connected in series. An intermediate re-pressurization chamber 98 may also be used between multiple fluidic pumps 60, 85.

Vacuum pumps 75 of the present disclosure may be variable displacement pumps, such as piston pumps, rotary screw pumps, or rotary vane pump, or fixed displacement pumps, in the case of multi-stage regenerative blowers. Cold traps of the present novel technology may also result in pressure gradients and function as vacuum pumps. Cold traps may be electrically cycled, or may be fed using cryogenic media, such as dry ice or liquid nitrogen.

Fluid flow may be regulated by modulating valve cross-sectional area, or by repeatedly opening and closing the valve. Automated valves may be energized, such as pneumatically or electrically, and controlled by a PLC in operational communication with a digital pressure meter.

A fluid inlet nozzle may be connected in fluidic communication with inlet port 30 to direct the flow of the liquid into the vessel 45. The liquid may flow directly along the gravitational path or may flow in a helical manner as it proceeds down an interior vessel wall. Helical paths may be used to increase retention time and disrupt the surface tension of the fluid, and may benefit from a nozzle 99 with a narrowing throat to increase velocity prior to injection resulting in increased retention times for longer exposure to vacuum conditions. The terminal end of a fluid inlet nozzle 30 may be located sufficiently close to a vessel wall 105 to prevent droplet formation and splashing, with typical distances less than fifteen centimeters and typically less than two centimeters from the vessel wall 105. Laminar flow inlets may be used to decrease splashing and volatilization occurring during injection. Alternatively, a single or a plurality of liquid inlet openings 30 may enable a quasi-uniform flow of liquid to sheet along the inner wall of the vessel 45 to the liquid outlet port 40.

Figure 5A:
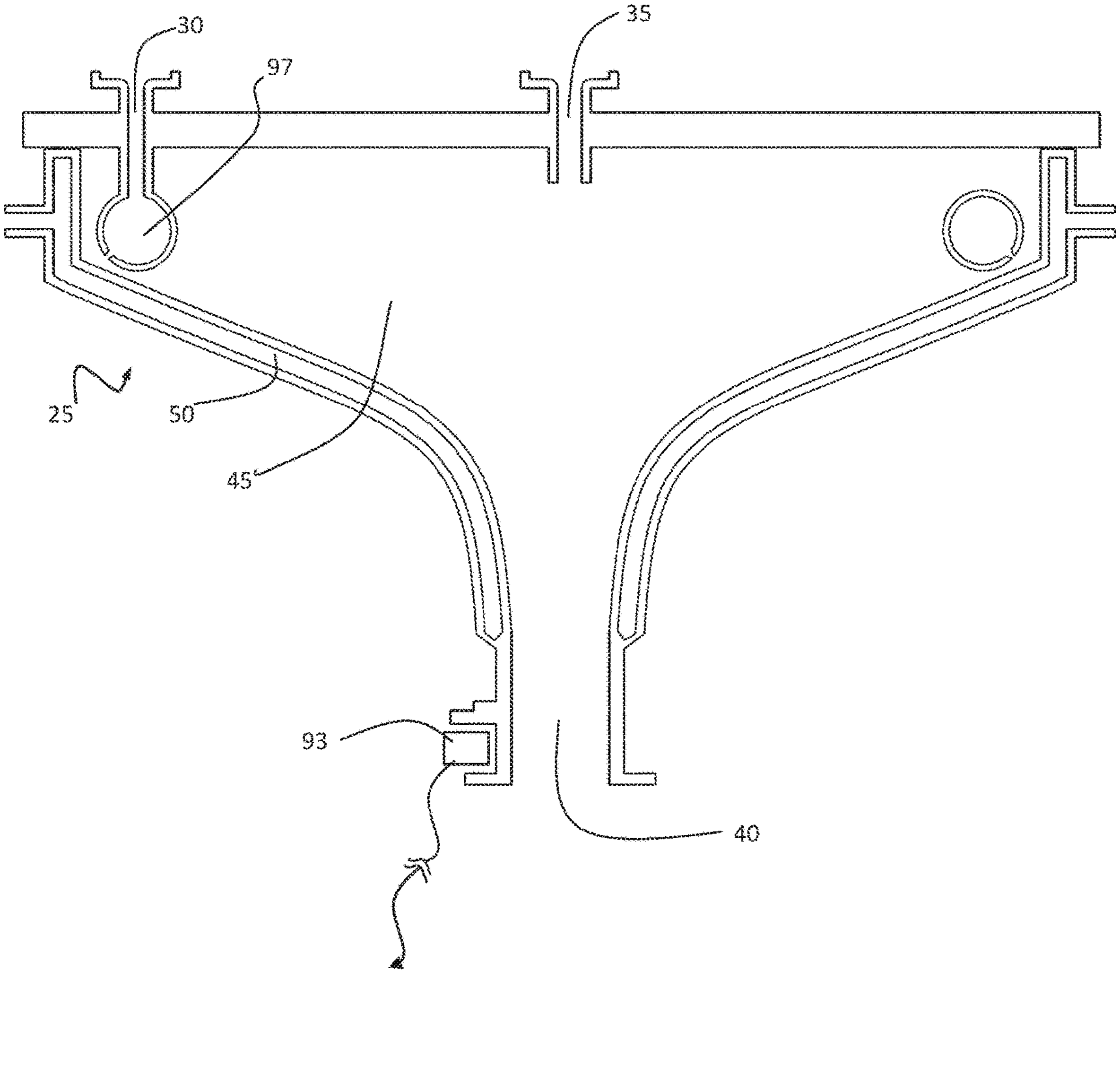
FIG. 5A is a cutaway view of pressure vessel of the embodiment of FIG. 4A wherein the vessel has concave interior sidewalls and features a fluid inlet body (manifold).
Figure 5B:
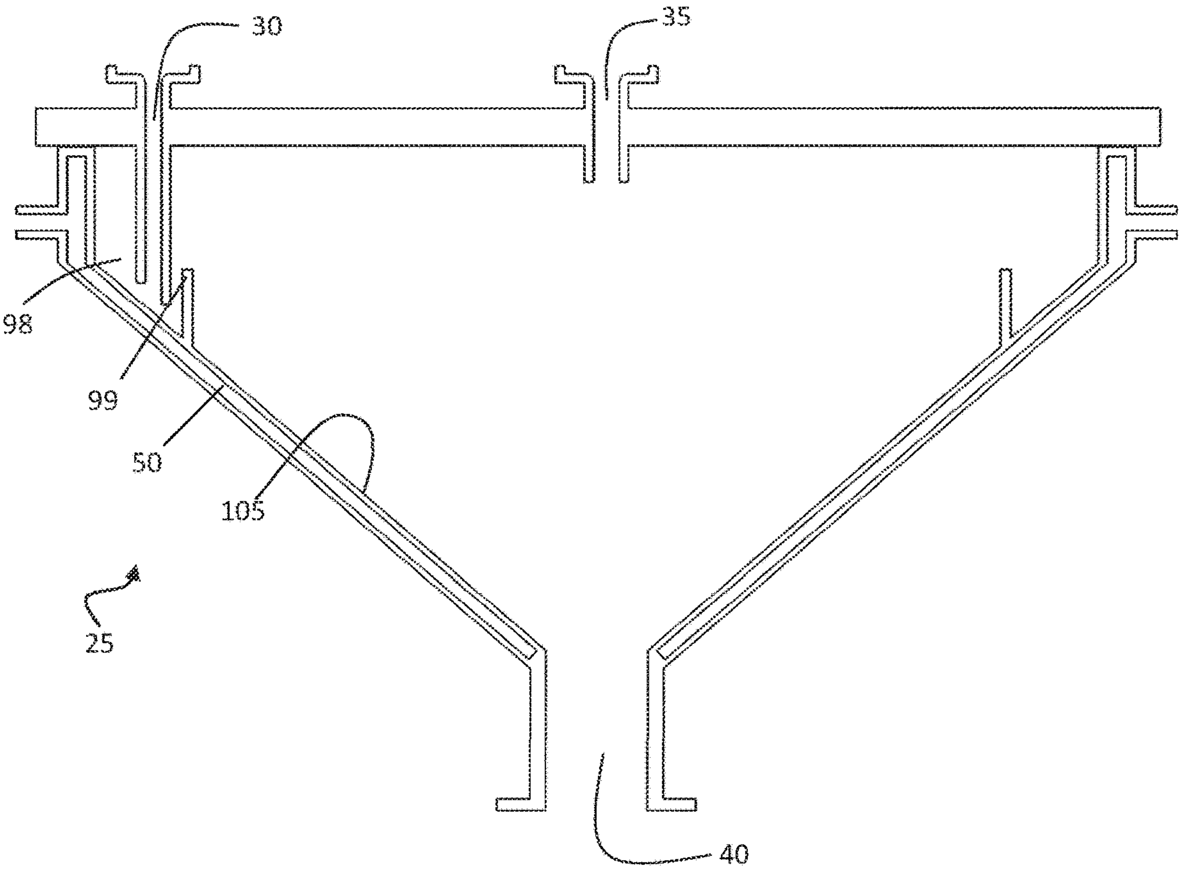
FIG. 5B is a cutaway view of pressure vessel of the embodiment of FIG. 4A wherein the vessel has an inlet trough operationally connected to the inlet port.
Figure 6B:
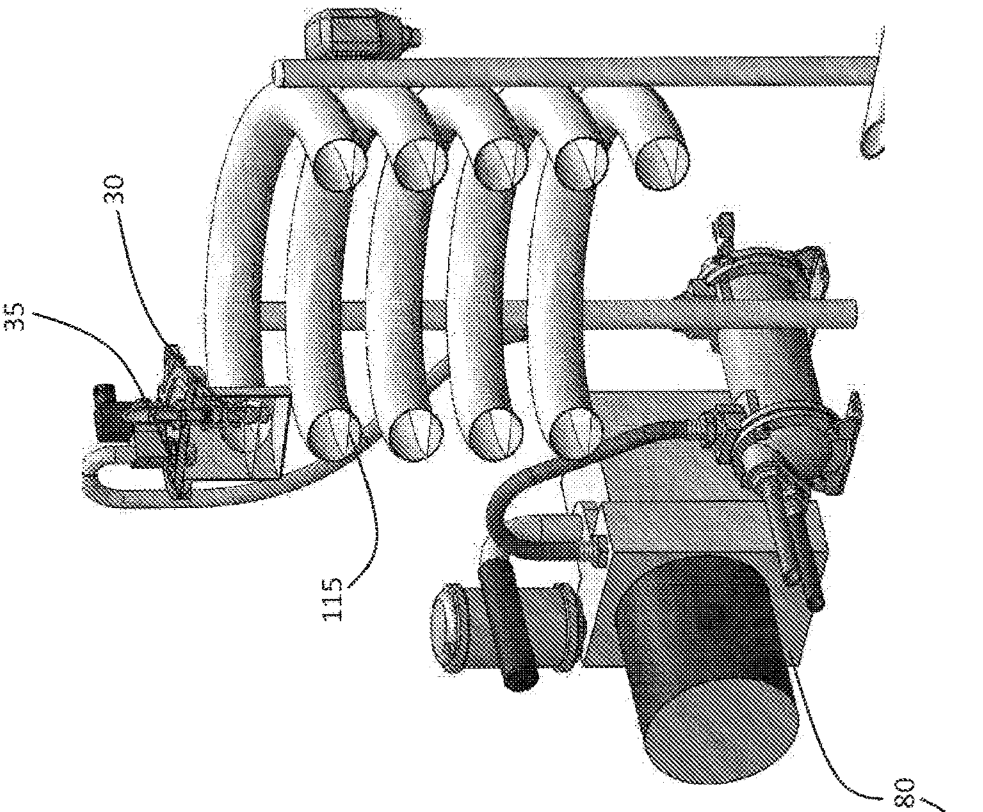
FIG. 6B is a cutaway view of the embodiment of FIG. 6A.
Figure 6A:
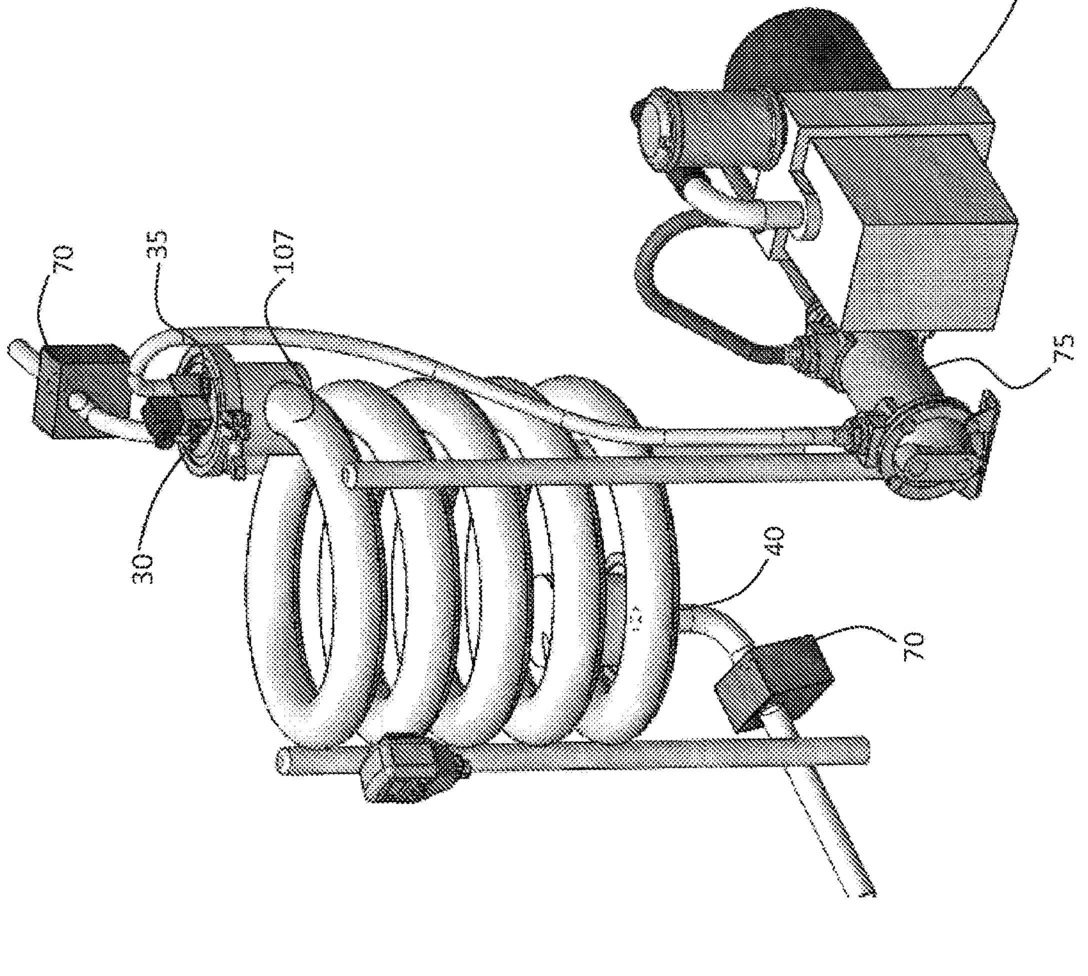
FIG. 6A is perspective view perspective view of a coffee rehabilitation system according to a fifth embodiment of the present invention.
Figure 7:
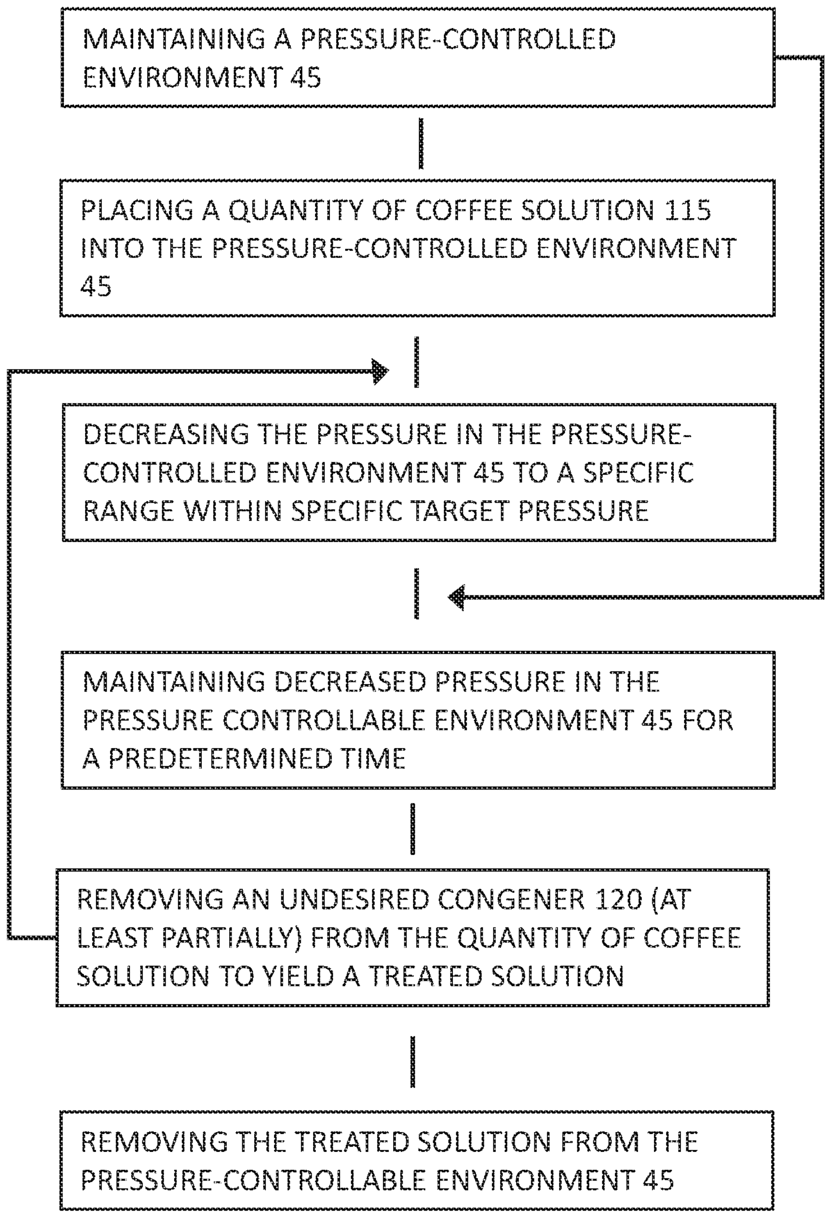
FIG. 7 is a schematic view of a method for rehabilitating coffee underlying the operation of the present embodiments.
Figure 8:
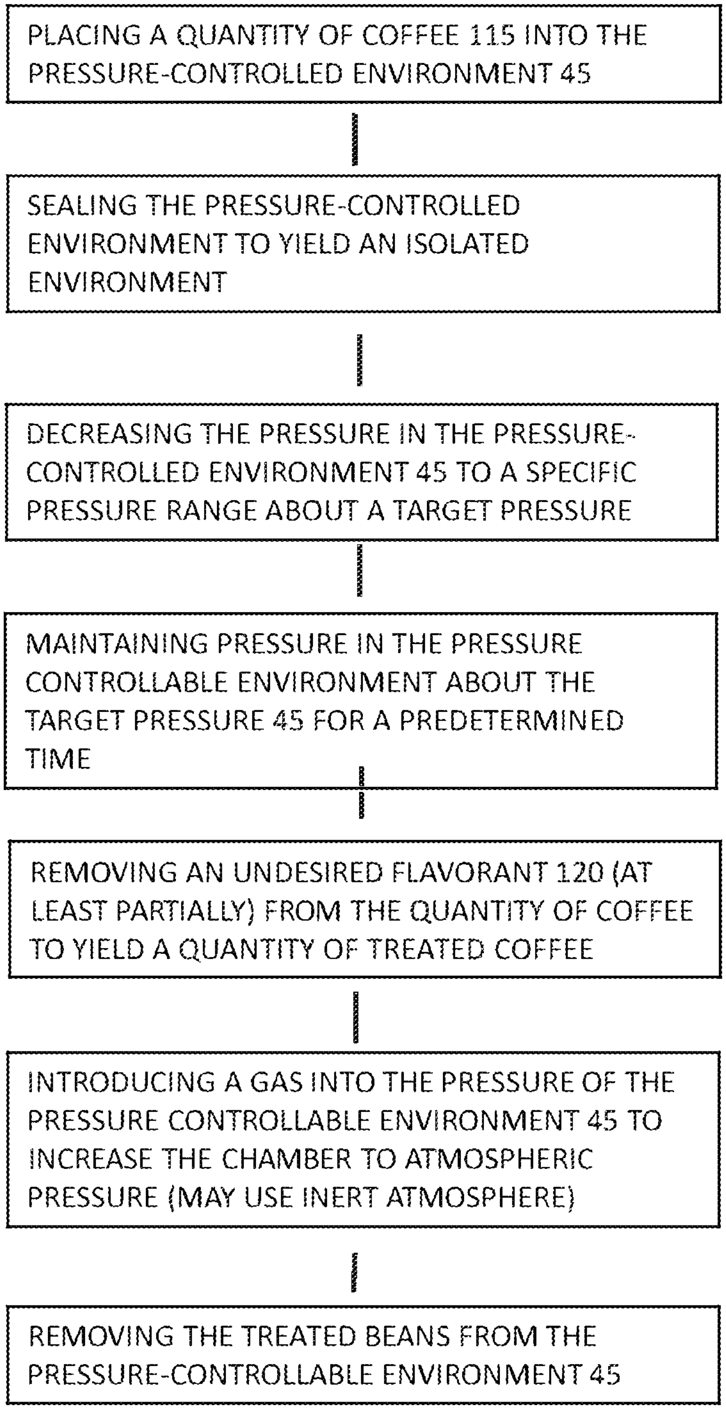
FIG. 8 is a schematic view of a method for rehabilitating coffee beans underlying the operation of the present embodiments.
Figure 9C:
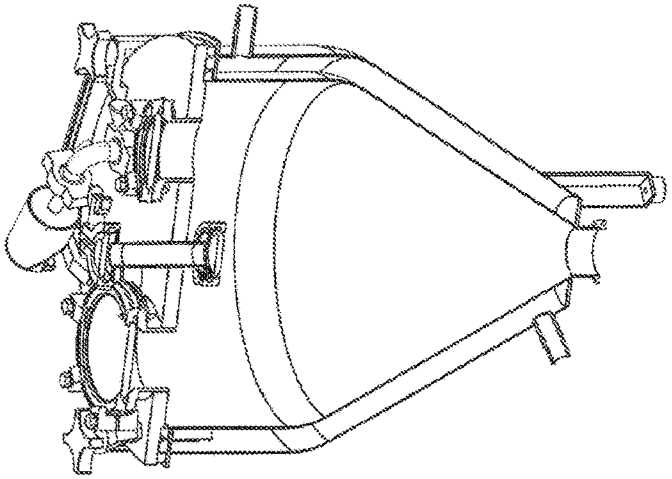
FIG. 9C is a cutaway view of the embodiment of FIG. 9B in a closed-lid orientation.
Figure 9B:
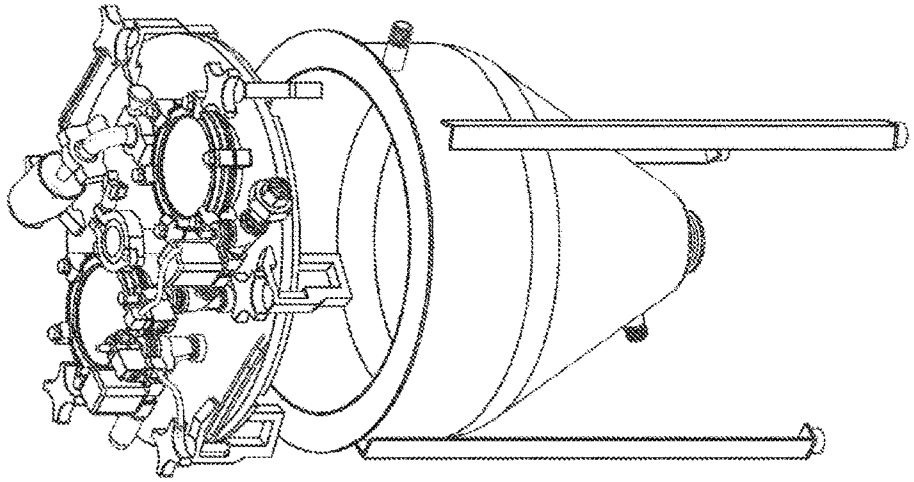
FIG. 9B is a perspective view perspective view of a coffee rehabilitation system according to the fifth embodiment of the present invention.
Figure 9A:
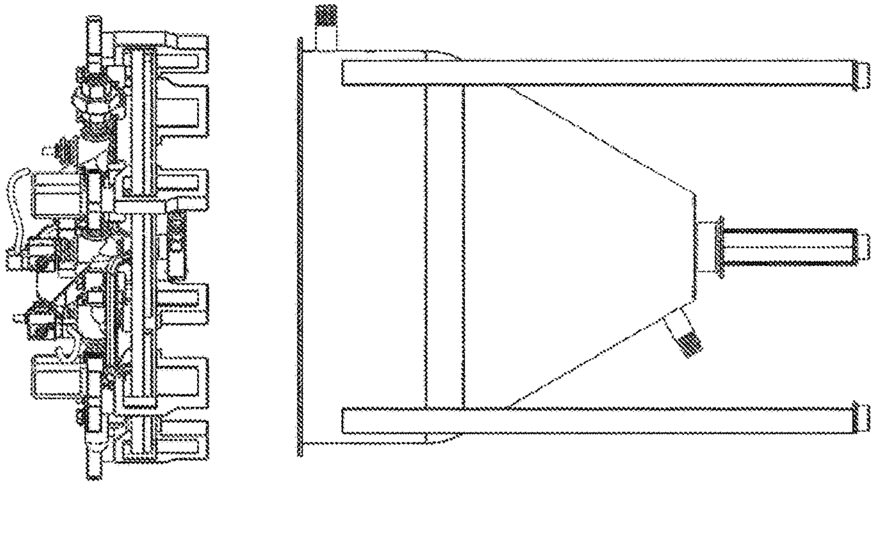
FIG. 9A is a front view perspective view of a coffee rehabilitation system according to the fifth embodiment of the present invention.

A liquid inlet body 97 may be used to decrease the pressure drop between a pressure regulator and vacuum vessel 45 by enabling liquid accumulation prior to injection (see FIG. 5A). In this case, liquid enters a manifold 97 a volume of space, such as a large tube, at least partially encircling the upper lip of the vessel 45. The cross-sectional area of the inlet body 97 is large relative to the inlet valve 31 enabling fluid to partially decrease in pressure prior to entering the vessel 45, which enables lower head pressures and slower flow. In another embodiment the liquid inlet body 97 may comprise bilateral pieces that may or may not be incorporated into the lid of the vessel. Bilateral separation may be used to enable rapid disassembly.

Example 5

FIGS. 9A-13 illustrate embodiments wherein coffee beans are introduced into the vessel in discrete predetermined amounts, such as through a rotating airlock hopper (FIG. 9A-9B) or a trap door hopper (FIGS. 10A-10C, 12 and 13). As in the previous examples, the vessel is pressure controllable through a gas outlet port connectable to a vacuum source.

Figure 13B:
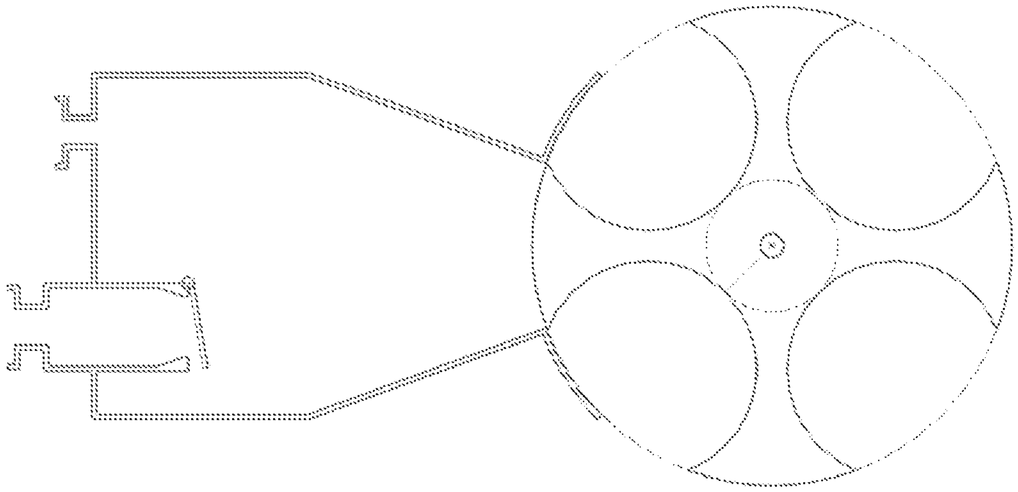
FIG. 13B is a perspective view of the coffee rehabilitation system of FIG. 13A.
Figure 13A:
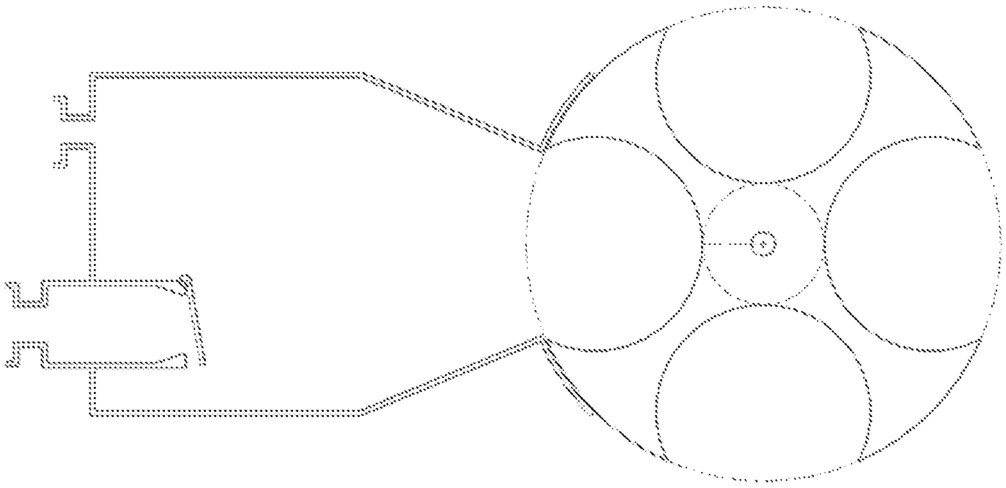
FIG. 13A is a perspective view of a coffee rehabilitation system according to a seventh embodiment of the present invention, illustrating a batch process with rotating discharge lock.
Figure 14C:
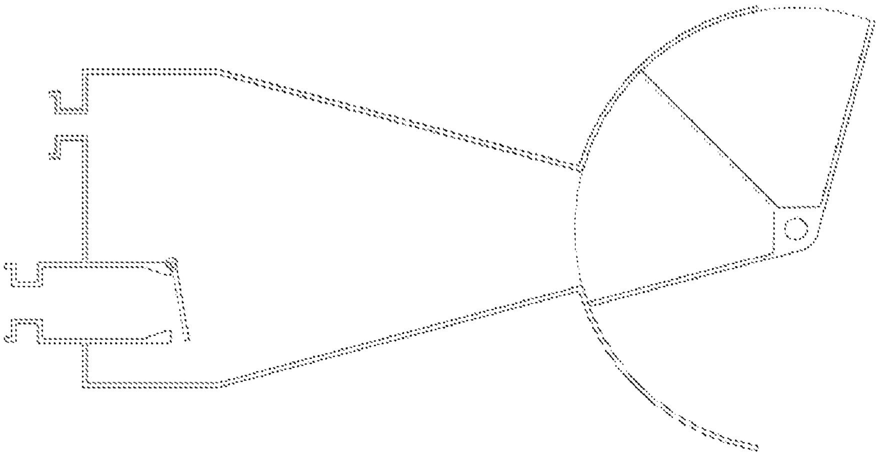
FIG. 14C is a perspective view of the coffee rehabilitation system of FIG. 14C.
Figure 14B:
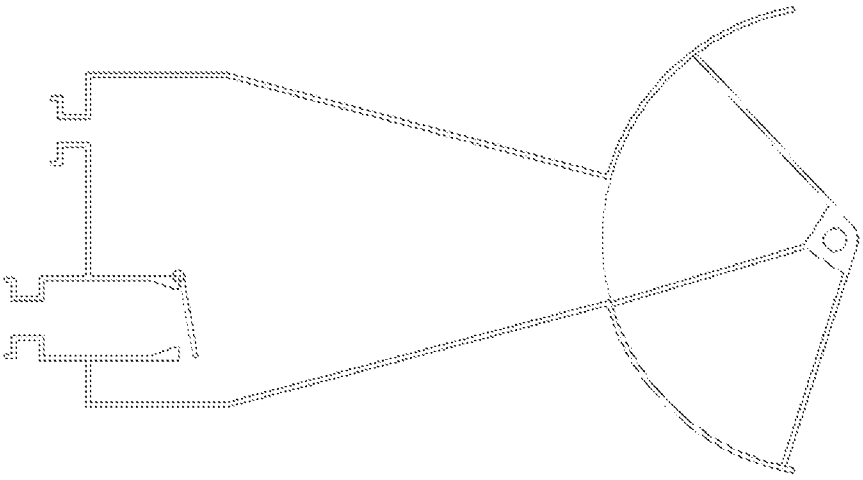
FIG. 14B is a perspective view of the coffee rehabilitation system of FIG. 14A.
Figure 14A:
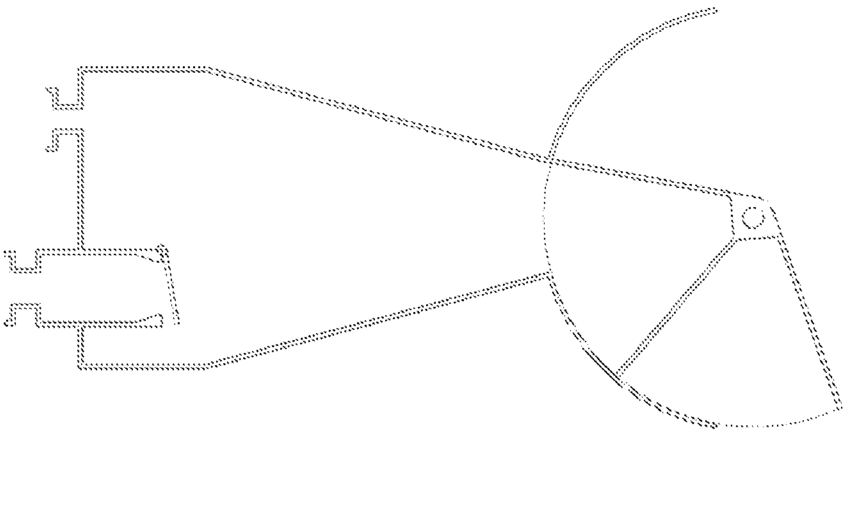
FIG. 14A is a perspective view of a coffee rehabilitation system according to an eighth embodiment of the present invention, illustrating a batch process with tilting discharge.
Figure 15B:
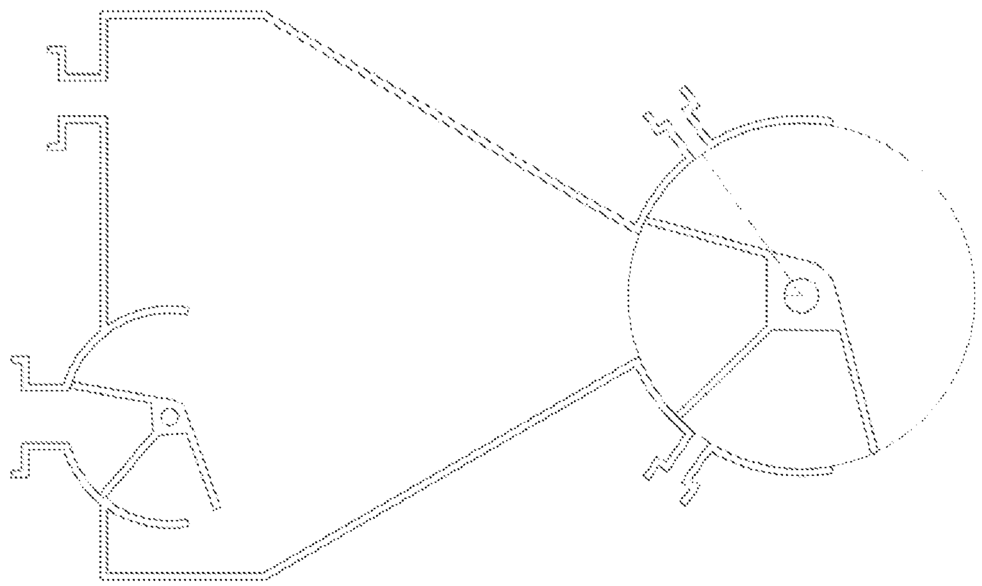
FIG. 15B is a perspective view of the coffee rehabilitation system of FIG. 15A.
Figure 15A:
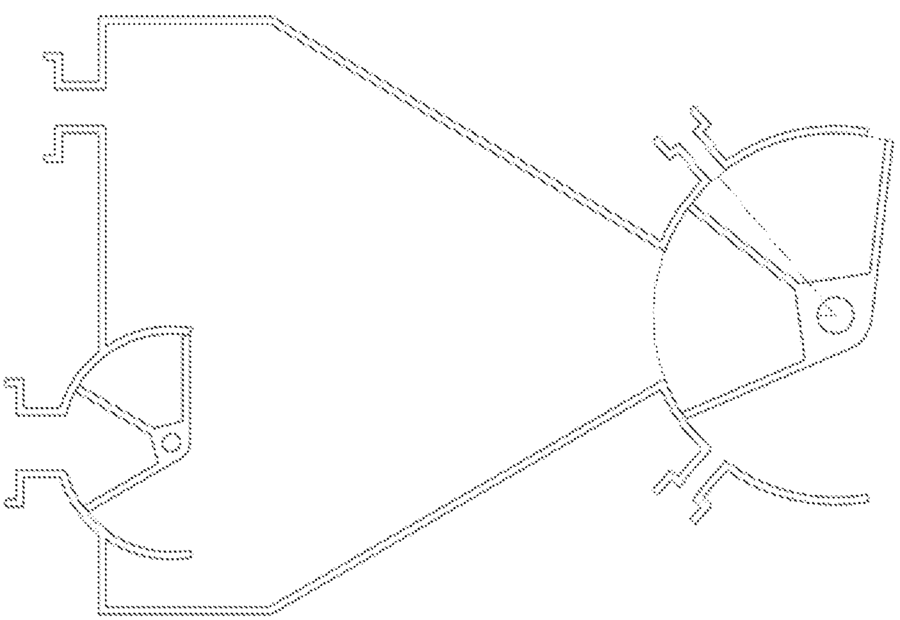
FIG. 15A is a perspective view of a coffee rehabilitation system according to a ninth embodiment of the present invention and illustrates a quasi-continuous tilting chamber with inert gas flush.
Figure 16B:
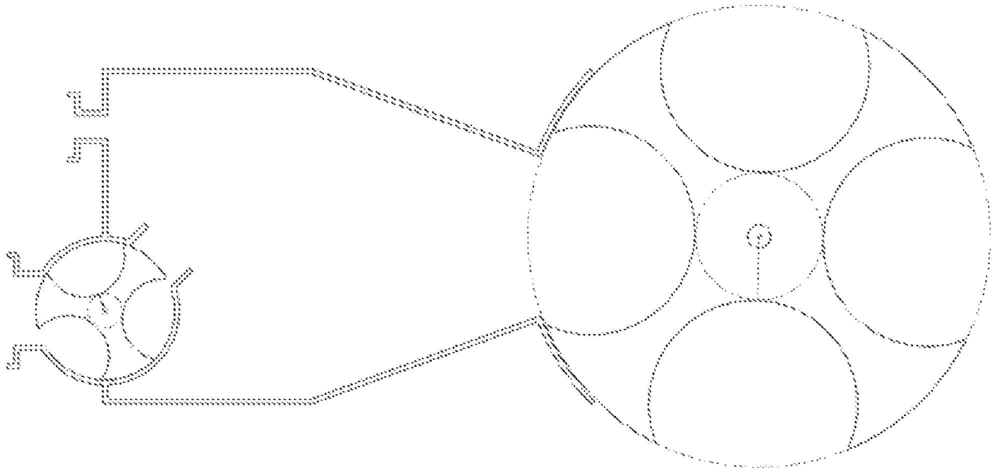
FIG. 16B is a perspective view of the coffee rehabilitation system of FIG. 16A.
Figure 16A:
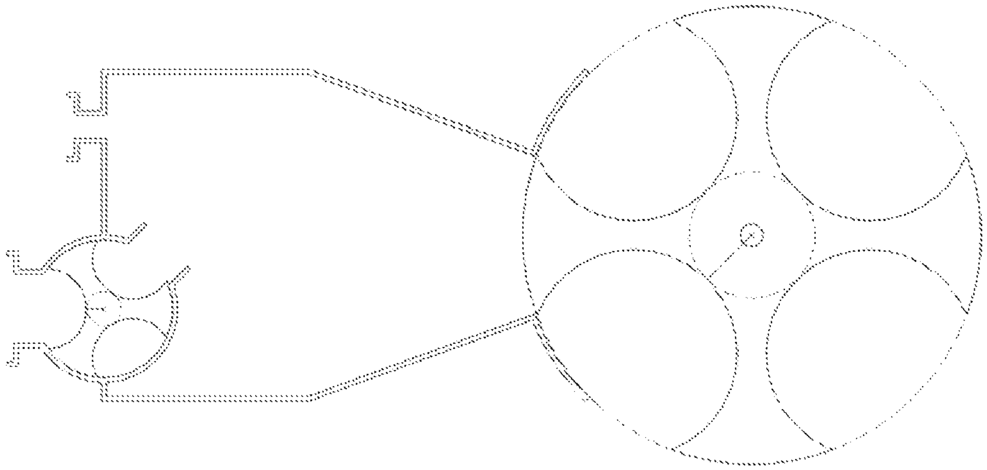
FIG. 16A is a perspective view of a coffee rehabilitation system according to a tenth embodiment of the present invention and relates to a quasi-continuous chamber aligned to dispense first lock.
Figure 17:
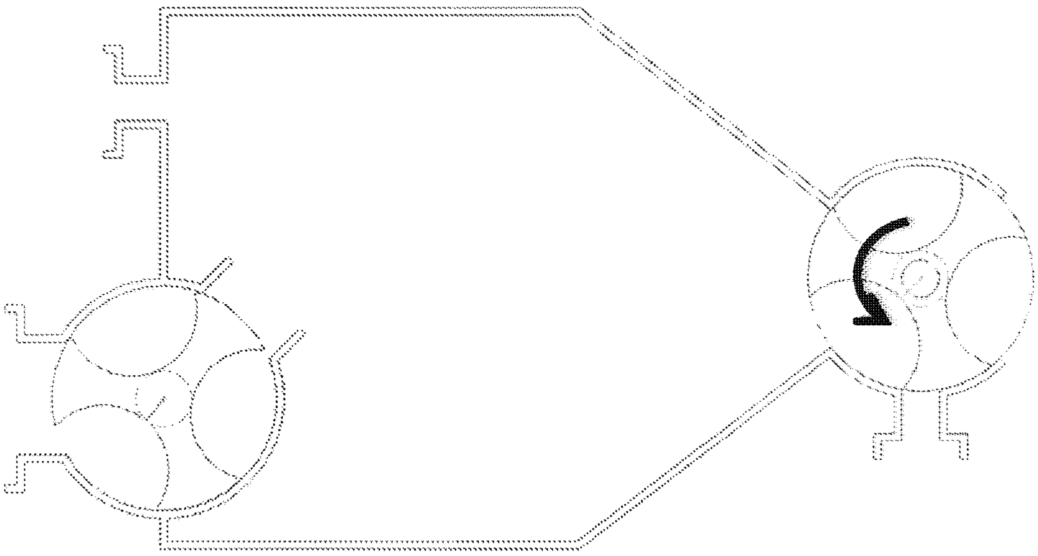
FIG. 17 is a perspective view of a coffee rehabilitation system according to an eleventh embodiment of the present invention, a quasi-continuous vertical axis dual lock rotating inlet and outlet with inert gas flush on outlet.
Figure 18:
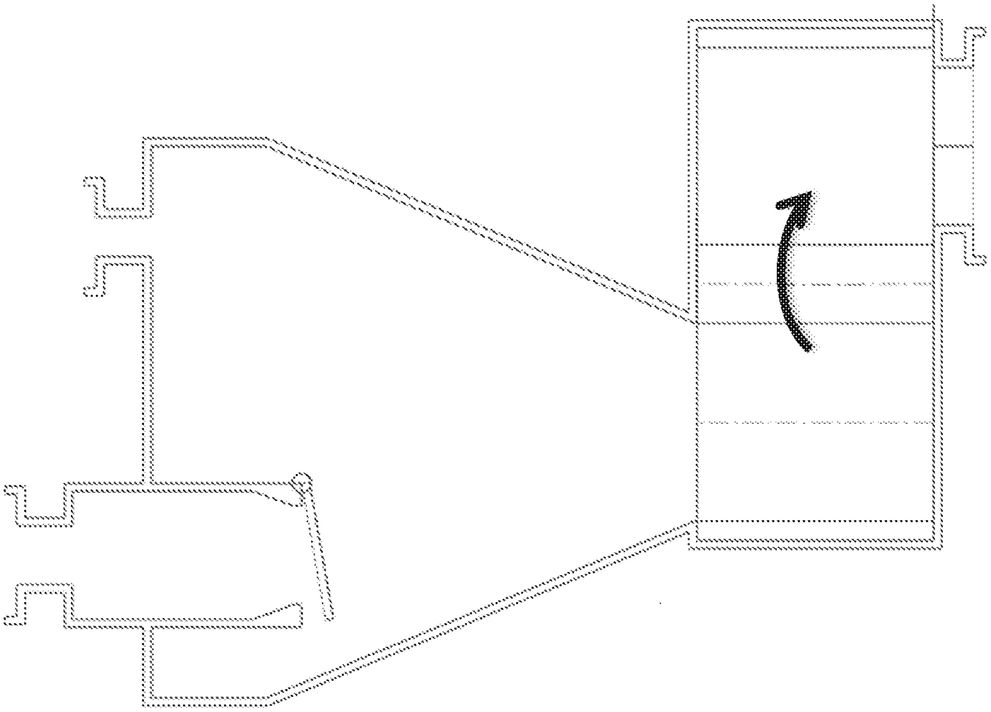
FIG. 18 is a perspective view of a coffee rehabilitation system according to a twelfth embodiment of the present invention and relates to a quasi-continuous horizontal axis rotating chamber.
Figure 19:
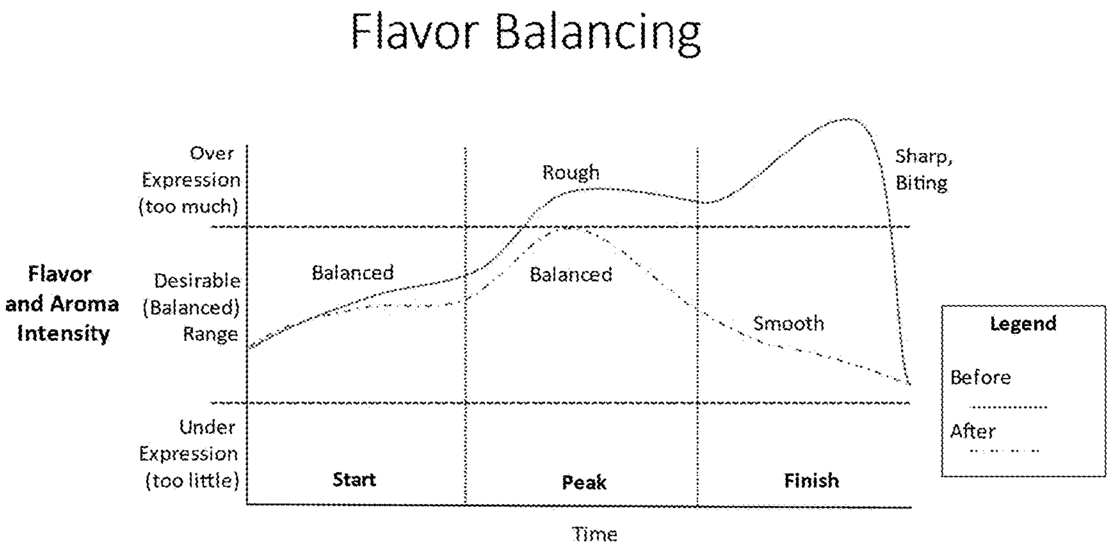
FIG. 19 graphically illustrates the organoleptic property of flavor balancing in terms of flavor/aroma intensity as a function of time.
Figure 20:
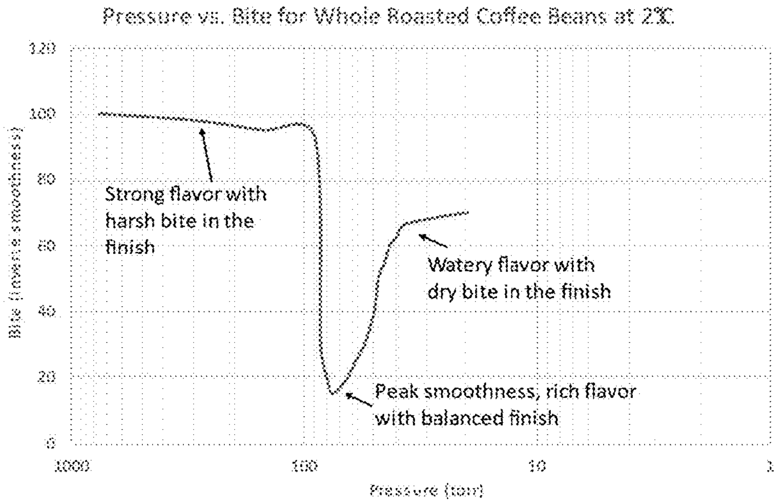
FIG. 20 graphically illustrates inverse smoothness of roasted coffee beans as a function of treatment pressure.
Figure 21:
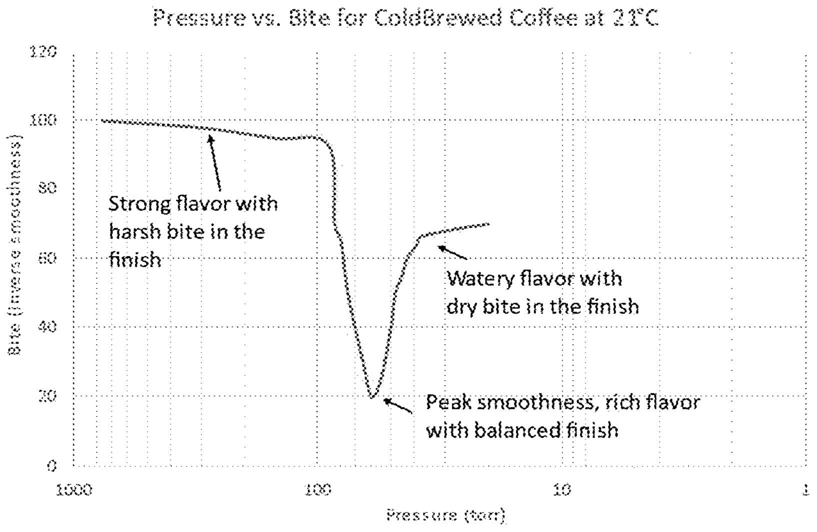
FIG. 21 graphically illustrates inverse smoothness of a coffee beverage as a function of treatment pressure.

In some embodiments, the vessel empties into a rotatable/pivotable exit airlock hopper (FIGS. 9A-9B, 10A-10C, 13, 15A-15B, 16A-16B, 17, 18) or a trap-door hopper (FIGS. 12, 14A-14C) which discharges treated coffee beans for collection. In the embodiment of FIG. 13, the vessel empties into a turntable chamber which may then be rotated to empty into a receiving container while another chamber is rotated into place in communication with the pressure vessel to receive the next batch of coffee to be treated, with the pressure vessel maintaining a partial vacuum from batch to batch.

FIGS. 11A-11B illustrate a batch treatment system having a hinged lid covering a pressure vessel into which a container of beans may be placed for treatment. The lid may be closed and sealed and a vacuum drawn in the vessel through a vacuum port in communication with the vessel and a vacuum source. After treatment, the treated beans may be removed for packaging and transport.

In the above batch embodiments, the coffee is typically introduced as a predetermined quantity of coffee beans; these beans are typically roasted, as roasted beans are more porous, but may also be introduced as green coffee beans.

In some embodiments, the inlet body 97 is maintained at a higher pressure, such as above ninety-five Torr, while the vessel is maintained at a lower pressure, such as between about thirty-five and ninety Torr. In this case pressure may be substantially decreased without significantly altering the liquid composition prior to entering the bulk vessel volume. Inlet body 97 may be maintained at pressures such as 760 Torr, 700 Torr, 500, Torr, 400 Torr, 200 Torr, 100 Torr, 95 Torr, or the like. The vessel 45 may be maintained at pressures such as 80 Torr, 75 Torr, 70 Torr, 65 Torr, 55 Torr, 45 Torr, or the like, typically for a period of 5 seconds.

A separate pressure drop vessel may be used to gradually step the pressure of the liquid down prior to entering the vessel 45. Typically, the pressure drop vessel would be maintained at a higher pressure, such as above ninety Torr.

In another embodiment (FIG. 5B), liquid enters vessel and is collected in trough 98. Once trough 98 has filled, liquid will pour over the trough and sheet down the sidewalls 105 toward sump 49. The trough 98 may fill to a level defined by a lip 99 until it flows over the lip 99 forming a sheet of liquid across the vessel wall 105. Alternatively, the trough may also contain a gap at the junction with the sidewall resulting in a 'leaky' trough that would result in a uniform sheet of liquid forming along the sidewall as it drains from the bottom of the trough.

Vessel 25 may be constructed of metal, such as stainless steel, copper or aluminum, or plastic, such as polycarbonate, acrylic, or PETG, or a combination thereof. The liquid may directly contact the inner wall 105 of the vessel 45, or may contact a surface liner disposed within and either isolated from, or disposed against the vessel wall 105.

A water jacket 50 may be constructed of a bulk volume between the inner vessel wall and a partially encapsulating wall defining a single thermal zone, or may comprise multiple thermal zones. Multi-zone cooling may be fabricated through the use of bulkheads or pillow plate in the case of stainless steel.

The inner wall 105 of the vacuum chamber 45 may be smooth or even polished, or may be deliberately etched and roughened to promote the evolution of bubbles. A smooth vessel wall 105 will promote liquid flow during helical circulation, while a rough or etched surface may retard liquid flow and result in increased liquid retention times in the case of liquid following a gravitational trajectory along the vessel wall 105.

In another embodiment of the present invention, liquid flow is introduced uninterrupted from the inlet port 30 to the liquid sump 49 without contacting the vessel wall 105. In this case the liquid passes or falls straight through the vessel 45 unimpeded and is outgassed during decent.

In still another embodiment (see FIGS. 6A and 6B), pressure vessel 25 has the form of spiral tube, with liquid inlet and gas outlet ports at a first, typically elevated, end 107 and the liquid outlet 40 positioned at the opposite end 109. Liquid typically travels from one end 107 to the other 109 as urged by gravity.

In operation, a predetermined quantity of a coffee 115, such as coffee extract or coffee beans, is inlet into pressure chamber 45. Typically, the coffee 115 enjoys a high surface area-to-volume ratio during residence in the pressure chamber 45, such as in the form of coffee extract droplets or a thin sheet or ribbon, so that predetermined undesired congeners 120 may be more quickly and efficiently evolved therefrom.

The atmosphere in the pressure chamber 45 is below atmospheric pressure (i.e., a partial vacuum) to encourage the preferential evolution of one or more undesired congeners 120 from the coffee 115. The present system 20 takes advantage of complex intermolecular forces in coffee beans and coffee solutions at low temperatures and pressures. Furthermore, ethyl acetate in high concentrations is offensive; however, at lower concentrations it may be desirable. The present method enables the selective control over the amount of ethyl acetate removed based on the temperature and vacuum pressure for a given retention time. This selectivity occurs over a very narrow pressure range. As a result, artisans may reliably tune the level of ethyl acetate in alcoholic beverages to create a desired flavor profile. While this disclosure focusses on the removal of ethyl acetate, other undesirable congeners may be similarly removed by advantageous selection of the pressure and temperature conditions of the vacuum treatment. This evolution of undesirable congeners 120 takes advantage of the fact that while such congeners 120 have boiling points quite close to ethanol at atmospheric pressure, the same congeners 120 have boiling points substantially different from, and typically lower than, ethanol at reduced pressures and the presence of multiple congeners in solution effects the relative boiling points of the other congeners. Thus, exposure of the ethanol solution to reduced pressures (partial vacuums) at particular temperature and pressure ranges allows for the preferential evolution of certain congeners 120, such as ethyl acetate, leaving behind the ethanol with certain desired lower boiling point congeners still in solution therewith (see FIG. 8).

In the case of a batch treatment, the liquid coffee solution 115 is loaded into the pressure chamber 45, the pressure chamber 45 is sealed pressure tight, and the pressure therein is reduced to the desired partial vacuum pressure. In the case of continuous flow treatment, the pressure within the pressure chamber 45 is maintained at the desired partial vacuum pressure and the coffee solution 115 is flowed therethrough at a predetermined desired rate.

Figure 10B:
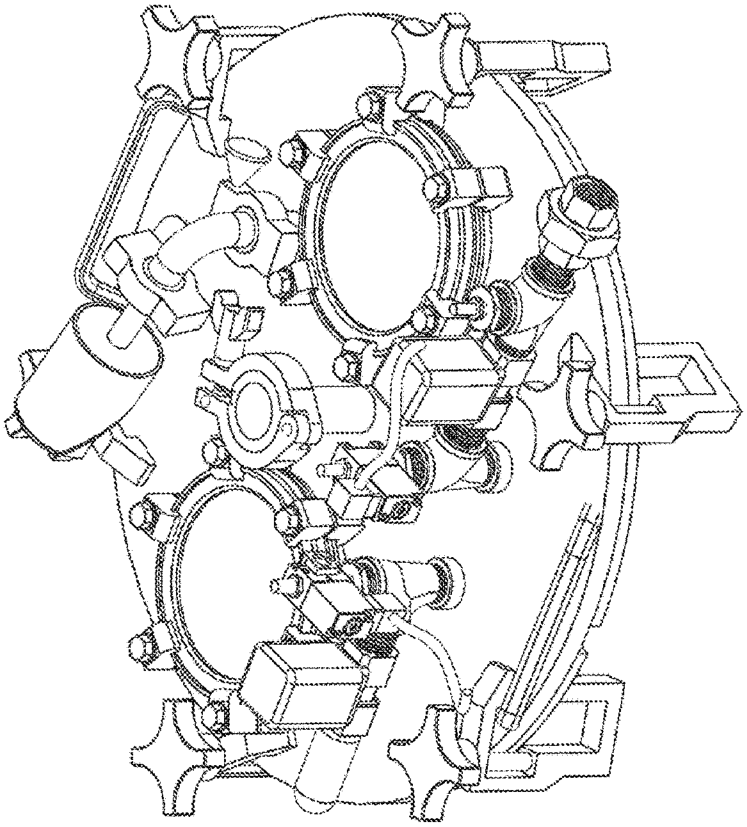
FIG. 10B is a perspective view perspective view of a lid of a coffee rehabilitation system according to the fifth embodiment of the present invention.
Figure 10A:
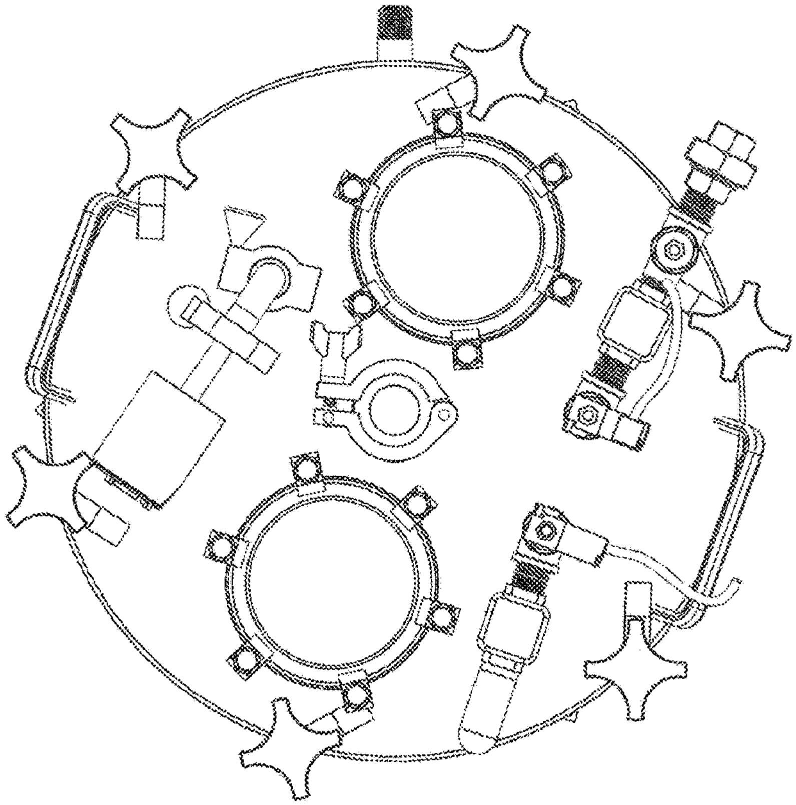
FIG. 10A is a top view perspective view of a lid of a coffee rehabilitation system according to the fifth embodiment of the present invention.
Figure 11:
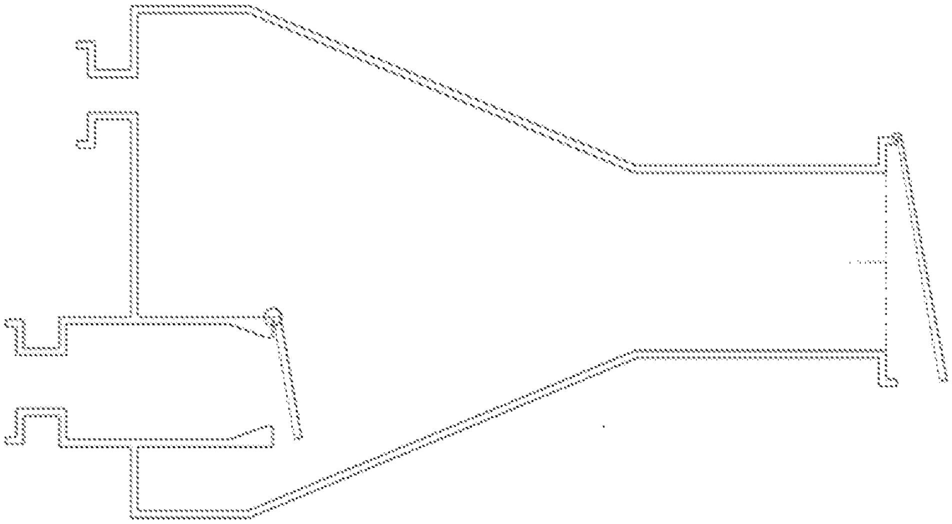
FIG. 11 is a perspective view of a coffee rehabilitation system according to the fifth embodiment of the present invention illustrating a batch process with dual static locks.
Figure 12C:
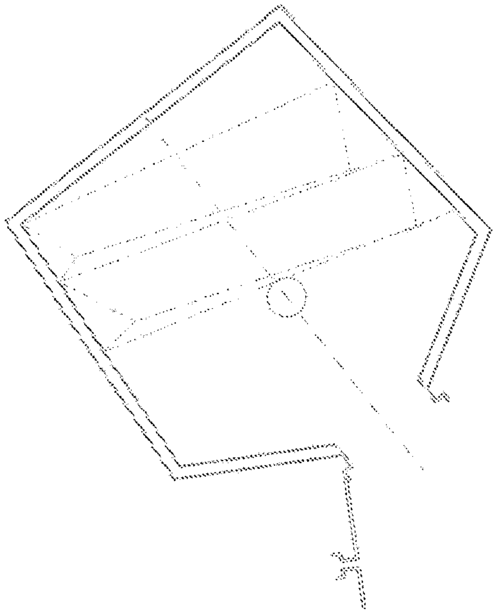
FIG. 12C is a perspective view of the coffee rehabilitation system of FIG. 12A.
Figure 12B:
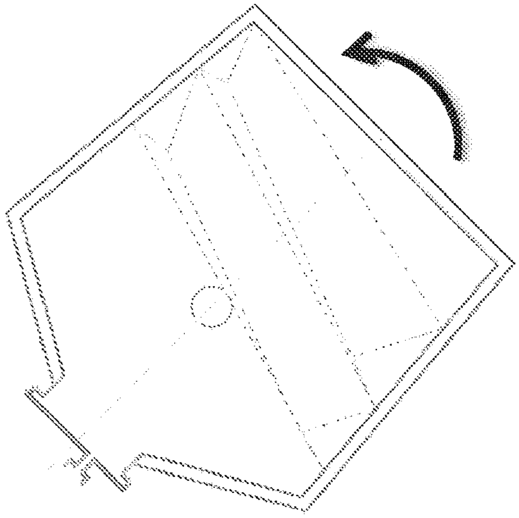
FIG. 12B is a perspective view of the coffee rehabilitation system of FIG. 12A.
Figure 12A:
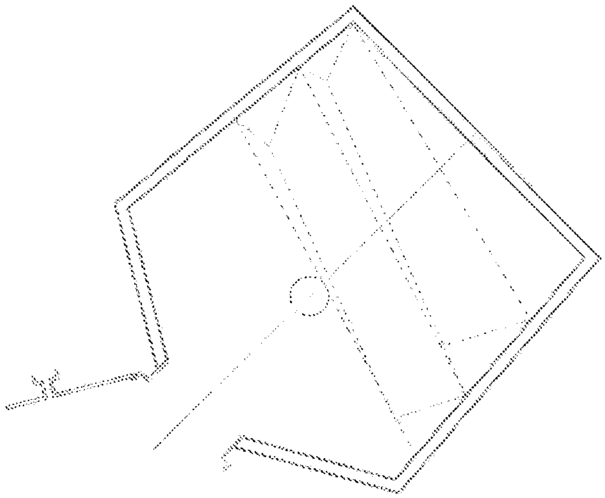
FIG. 12A is a perspective view of a coffee rehabilitation system according to a sixth embodiment of the present invention and illustrates a batch chamber with single static seal and rotating mixing paddles showing tilt charging.

The above treatment may be fine-tuned by varying parameters such as treatment partial pressure, temperature, time at minimum pressure, pressure ramping profiles (both decreasing and increasing), and the like, individually and in combination, to effect desired resulting changes in coffee flavor, acidity, aroma, focus on specific congeners, and the like. Typically, vessel pressure is regulated to within a precision range of +/−five (5) Torr, more preferably +/−three (3) Torr, still more preferably +/−two (2) Torr, yet more preferably +/−one (1) Torr, and even still more preferably +/−one-half (0.5) Torr. Referring to FIGS. 10A-10B, a precision pressure control system is illustrated. The precision pressure control system includes a pressure vessel lid for airtight connection to a pressure vessel defining a pressure seal. The lid has a pressure sensor operationally connected for connection in pneumatic communication with the pressure vessel when the lid is securely connected thereto. Likewise, the lid includes an inlet port for passing coffee into the pressure vessel, a first coarse/fine variable control valve operationally connected in pneumatic communication with the vessel and connectable to an air or flushing gas source, and a second coarse/fine variable control valve operationally connected in pneumatic communication with the vessel and connectable to a vacuum source. The valves may be connected to an electronic controller and energized by signals therefrom, typically in response to signals form one or more pressure and/or temperature sensors in the pressure vessel.

Likewise, the vessel temperature may be varied between about negative twenty (−20) to about ninety (90) degrees Celsius during treatment, with the temperature profile typically varying with the pressure profile, and with the treatment temperatures for whole beans being somewhat higher than for liquid extracts. In general, for a given congener, the liquid temperature may vary from about negative twenty degrees Celsius to about eighty degrees Celsius, more typically from about zero degrees Celsius to about sixty degrees Celsius, still more typically from about ten degrees Celsius to about thirty-five degrees Celsius; similar ranges offset at between about ten and fifteen degrees higher are typical for the treatment of solid beans.

In some embodiments the vacuum systems include a valve assembly that allows for both course and fine vacuum control, enabling an electronic controller to maintain pressure within the vessel according to a predetermined pressure profile. The pressure may be maintained to withing the tolerances discussed above, and may be ramped up and down and/or held constant according to predetermined pressure profiles. Likewise, predetermined pressure/temperature profiles may be followed and maintained over a period of time.

In some embodiments, the pressure vessel may be a rotating and/or tilting drum vacuum system, allowing for better homogenization of vacuum treatment of the so-loaded coffee material. By tilting and/or rotating the vessel, the coffee material is better distributed and treatment of the same is better homogenized. This embodiment is especially useful for treating large (commercial) quantities of coffee beans at once.

In some embodiments, after the vacuum treatment the treated coffee is exposed to an inert atmosphere flush back to ambient pressure, such as with nitrogen, argon or the like. Such an inert atmosphere flush following a vacuum purge tends to fill up the pores in coffee beans to prevent unintended oxidation of the congeners after vacuum treatment.

In many of the above examples, the goal is the adjustment of congener levels, both absolute and relative to one another. In these examples, by holding the atmosphere in the pressure chamber at ambient temperature and at a reduced pressure (such as sixty to eighty-five Torr, more typically sixty-five to eighty Torr, still more typically sixty-five to seventy-five Torr, and yet more typically about seventy Torr), ethyl acetate may be substantially removed from a coffee solution 115 without substantially decreasing the coffee solution content of said solution 115. Residence time at maximum experienced vacuum (the 'process period'), typically about seventy Torr for flowing coffee solution 115, is typically no more than about ninety seconds, more typically no more than about sixty seconds, still more typically no more than about twenty seconds, and yet more typically no more than about five seconds. In the case of the batch style assembly apparatus, residence time at maximum vacuum for the coffee (beans and/or solution) 115 may be a bit longer, but still no more than a few minutes. Moreover, as the vacuum partial pressure decreases and/or the temperature increases, residence time of the coffee solution 115 may likewise decrease. In general, for a given congener, the temperature may vary from about negative twenty degrees Celsius to about eighty degrees Celsius, more typically from about zero degrees Celsius to about sixty degrees Celsius, still more typically from about ten degrees Celsius to about thirty-five degrees Celsius.

In many of these embodiments, the coffee solution 115 remains liquid throughout the vacuum treatment process and throughout exposure to the reduced pressure environment in the pressure chamber 45. While the evolved congeners 120 change phase from liquid to gas the coffee solution remains liquid, meaning that there is no distillation and/or recondensation or reconstitution of the coffee solution 115 during processing in the pressure chamber.

Many of the typically undesirable congeners have very similar boiling points as do the desired congeners, and the coffee solution itself, at atmospheric pressure, but have dissimilar boiling points at reduced pressures, wherein they exhibit significantly lower boiling points. By maintaining a pressure of between sixty and eight-five Torr, and typically around seventy-five Torr, in the pressure chamber 45 and controlling the temperature within the pressure chamber 45 (typically around about twenty-two degrees Celsius), unwanted congeners, such as ethyl acetate, may be preferentially or substantially completely removed from coffee solution leaving substantially all of the coffee solution therein. It should be note that the liquid environment has an effect on the pressure range under which ethyl acetate in particular, and other congeners in general, may be selectively removed. In some liquid environments, lower pressures are required to remove congeners such as ethyl acetate, while in other environments ethyl acetate is removed at higher pressures.

Typically, at least one third of the unwanted congener is removed, more typically at least one half is removed, still more typically at least two-thirds is removed, and yet more typically substantially all the ethyl acetate is removed from the coffee solution. As used herein, preferentially removing an unwanted congener means removing some or all of the unwanted congener from solution without substantially removing any of the other constituents of the solution.

Looked at another way, the typical coffee solution beverage has between about 0.05 percent and 0.25 percent, or greater, content of any given unwanted congener. The instant coffee rehabilitation treatment typically reduces that amount to about fifty percent or less of the original unwanted congener content, sometimes by as much as about ninety-five percent. The target amount is determined by a number of factors, including personal taste and type of coffee beverage. A good rule of thumb is to reduce the unwanted congener content to about half the original content, or to between forty and sixty percent. All values are given as weight percent, and water content is ignored such that all values relate to the coffee solution distillate fraction of the overall coffee solution.

By selecting other treatment temperature/pressure/residence time combinations, other congeners my likewise be selectively removed. In some embodiments, temperature sensors and/or pressure sensors and/or chemical sensors (or combinations of the same) are positioned in thermal communication with the interior of the vessel 25 and/or the water jacket and/or the vapor outlet port (or combinations of the same). These sensors may be operationally connected to an electronic controller that may likewise be connected to one or more of the pumps 60, 75, 85 and/or ports 30, 35, 40 and/or valves 70 and/or agitators 95 (if present) to provide feedback-based control of the process to maintain the process within predetermined parameters and/or within predetermined pressure/temperature profiles. In some embodiments, the temperature and pressure within the chamber may be varied during residence of the coffee solution 115 to selectively target and remove a plurality of undesired congeners 120; this technique would likely apply best to a batch treatment. In other embodiments, the coffee solution 115 may be flowed sequentially through a plurality of pressure vessels 25, each having a pressure chamber 45 characterized by a different predetermined vacuum partial pressure and temperature to target one or more specific congeners 120.

One typically undesirable congener is ethyl acetate. The boiling point of ethyl acetate shifts with decreasing pressure. As shown in the drawings, the pressure range at which ethyl acetate may be selectively removed from a beverage may shift non-linearly with the environmental pressure on the beverage solution. By maintaining a pressure of between thirty-five and ninety Torr in the pressure chamber 45 and controlling the temperature within the pressure chamber 45 to be about twenty-two degrees Celsius, the ethyl acetate equilibrium concentration may be preferentially shifted for a coffee solution. It is interesting to note that the ambient liquid environment has an effect on the pressure range under which a given flavorant, in these examples ethyl acetate, is selectively removed. In a given vapor environment, the selective pressure range (about 40 torr to 80 Torr) may be lower than the range required to achieve an equivalent equilibrium shift of ethyl acetate concentration from another liquid, and higher than required to achieve an equivalent equilibrium shift of ethyl acetate from still another liquid.

The effect of reduced pressure treatment on beverage solutions may be better understood as a shift of equilibrium concentration of ethyl acetate rather than removal of the same through partial distillation. Consequently, solution retention time at reduced pressure may not cause ethyl acetate concentration to drop to zero. The solution might experience a little shift in congener concentration for a given retention time. Typically, at least one third of the ethyl acetate is removed, more typically at least one half is removed, still more typically at least two-thirds is removed, and yet more typically substantially all the ethyl acetate is removed from the beverage solution. As used herein, preferentially removing an unwanted congener, such as ethyl acetate, means removing some or all of the unwanted congener from solution without substantially removing any of the other constituents of the solution.

The instant rehabilitation treatment typically reduces that amount to about fifty percent or less of the original ethyl acetate content. The target amount is determined by a number of factors, including personal taste and type of coffee beverage. A good rule of thumb is to reduce the ethyl acetate content to about half the original content, or to between forty and sixty percent, and in some cases down to about three percent of the original content. All values in this paragraph are given as weight percent.

By selecting other treatment temperature/pressure/residence time combinations, other congeners my likewise be selectively removed. In some embodiments, temperature sensors and/or pressure sensors and/or chemical sensors (or combinations of the same) are positioned in thermal communication with the interior of the vessel 25 and/or the water jacket and/or the vapor outlet port (or combinations of the same). These sensors may be operationally connected to an electronic controller that may likewise be connected to one or more of the pumps 60, 75, 85 and/or ports 30, 35, 40 and/or valves 70 and/or agitators 95 (if present) to provide feedback-based control of the process to maintain the process within predetermined parameters and/or within predetermined pressure/temperature profiles. In some embodiments, the temperature and pressure within the chamber may be varied during residence of the coffee solution 115 to selectively target and remove a plurality of undesired congeners 120; this technique would likely apply best to a batch treatment. In other embodiments, the coffee solution 115 may be flowed sequentially through a plurality of pressure vessels 25, each having a pressure chamber 45 characterized by a different predetermined vacuum partial pressure and temperature to target one or more specific congeners 120.

While the novel technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

What is claimed is:

1. A method for rehabilitating coffee, comprising:

placing a pre-rehabilitated quantity of coffee in a pressure-controllable environment, the pre-rehabilitated quantity of coffee including an unprocessed concentration of at least one unwanted congener;

decreasing a pressure of the pressure-controllable environment to a reduced pressure;

holding the pressure of the pressure-controllable environment at the reduced pressure for a predetermined period of time;

during the predetermined period of time, removing the at least one unwanted congener from the pre-rehabilitated quantity of coffee to yield a treated quantity of coffee including a reduced concentration of the at least one unwanted congener, the reduced concentration being at most about two-thirds of the unprocessed concentration; and removing the treated quantity of coffee from the pressure-controllable environment;

wherein the reduced pressure is between about thirty-five Torr and about ninety Torr, and wherein the reduced pressure is maintained to within +/−2 Torr.

2. The method of claim 1, and further comprising:

after decreasing the pressure, cooling the pressure-controllable environment.

3. The method of claim 2 further comprising maintaining the pressure-controllable environment at about 10 degrees Celsius and about 35 degrees Celsius.

4. The method of claim 1, wherein the predetermined period of time is between about 5 seconds and about 90 seconds.

5. The method of claim 1, wherein the reduced concentration is about one-half of the unprocessed concentration.

6. The method of claim 1, wherein the reduced concentration is about one-third of the unprocessed concentration.

7. The method of claim 1, wherein the treated quantity of coffee is a mixture of water and a distillate fraction, and wherein the distillate fraction has a maximum unwanted congener concentration of about 0.05 weight percent.

8. The method of claim 1, wherein the treated quantity of coffee is a mixture of water and a distillate fraction, and wherein the distillate fraction has a maximum unwanted congener concentration of about 0.03 weight percent.

9. The method of claim 1 further comprising:

removing at least two unwanted congeners from the pre-rehabilitated quantity of coffee.

10. The method of claim 1 further comprising:

removing at least one different unwanted congener from the treated quantity of coffee to yield a re-treated quantity of coffee.

11. The method of claim 1 wherein the pre-rehabilitated quantity of coffee includes a plurality of coffee beans or a coffee solution.

12. The method of claim 1, wherein the pressure-controllable environment further comprises:

a pressure vessel defining a pressure controllable chamber;

a temperature regulator at least partially surrounding the pressure controllable chamber and in thermal communication therewith;

a liquid inlet port in fluidic communication with the pressure controllable chamber;

a gas outlet port in fluidic communication with the pressure controllable chamber;

a vacuum pump in fluidic communication with the gas outlet port;

a collection vessel configured to receive the treated quantity of coffee; and a liquid outlet port in fluidic communication with the pressure controllable chamber.

13. The method of claim 12 wherein the temperature regulator is a water jacket.

14. An apparatus for rehabilitating a coffee composition, comprising:

a pressure vessel defining a pressure controllable chamber that is configured to receive the coffee composition for rehabilitation through an inlet port of the apparatus, the pressure vessel extending along a first axis;

a water jacket at least partially surrounding the pressure controllable chamber and in thermal communication therewith;

a gas outlet port in fluidic communication with the pressure controllable chamber;

a vacuum pump in fluidic communication with the gas outlet port;

a collection vessel; and a rotatable discharge chamber that is in communication with the pressure controllable chamber and the collection vessel, the rotatable discharge chamber rotating about a second axis that is different than the first axis to empty the rehabilitated coffee composition received from the pressure controllable chamber into the collection vessel.

15. The apparatus of claim 14, wherein the coffee composition is a coffee beverage, the apparatus further comprising:

a coffee solution source operationally connected to the inlet port;

a first liquid pump in fluidic communication with the inlet port and the coffee solution source; and a second liquid pump in fluidic communication with the collection vessel and an outlet port that is in fluidic communication with the pressure controllable chamber.

16. The apparatus of claim 15 further comprising:

a helical race winding around the pressure controllable chamber a plurality of times from the inlet port to the outlet port.

17. The apparatus of claim 14 further comprising:

an agitator positioned in the pressure controllable chamber.

18. The apparatus of claim 14 further comprising at least one sensor operationally connected within the pressure controllable chamber, wherein the at least one sensor is selected from a group comprising pressure sensors, temperature sensors, chemical sensors, and combinations thereof.

19. The apparatus of claim 15 further comprising:

an electronic controller operationally connected to one or more of the first liquid pump, the second liquid pump, the inlet port, the outlet port, or the water jacket.

20. The apparatus of claim 14 further comprising a first pressure control valve operationally connected between the vacuum pump and the gas outlet port, wherein the first pressure control valve may be actuated to maintain a desired vacuum chamber pressure within a precision range of +/−2 Torr.

21. A method for removing at least one unwanted congeners from a coffee solution including an unprocessed amount of the at least one unwanted congeners, comprising:

establishing a partial vacuum in a pressure vessel for a period of time between about 5 seconds and about 90 seconds;

flowing a quantity of coffee solution into the pressure vessel; and during the period of time, preferentially removing at least a third of the at least one unwanted congener relative to other congeners of a group of congeners from the coffee solution to yield a treated coffee solution;

wherein the coffee solution in the pressure vessel remains liquid, and wherein the partial vacuum is between about 35 Torr and about 90 Torr.

22. The method of claim 21, wherein the at least one unwanted congener is removed at between about 10 degrees Celsius and about 30 degrees Celsius, and wherein the at least one unwanted congener includes ethyl acetate.

23. An organoleptically-improved beverage derived from a coffee composition using the method of claim 21, wherein:

the organoleptically-improved beverage comprises coffee; and the coffee composition from which the organoleptically-improved beverage is derived from possesses one or more undesirable organoleptic properties not found in the organoleptically-improved beverage, the coffee composition including a processed amount of ethyl acetate reduced by 10% to 97% of an unprocessed amount of ethyl acetate.

24. The organoleptically-improved beverage of claim 23, wherein one or more desirable organoleptic properties of the organoleptically-improved beverage are at least substantially similar to one or more corresponding desirable organoleptic properties of the coffee composition from which the organoleptically-improved beverage was derived.

25. The organoleptically-improved beverage of claim 23, wherein one or more desirable organoleptic properties of the organoleptically-improved beverage is substantially improved over one or more corresponding desirable organoleptic properties of the coffee composition from which the organoleptically-improved beverage was derived.

26. The organoleptically-improved beverage of any one of claims 23-25, wherein the one or more undesirable organoleptic properties is selected from the group consisting of harsh finish, sharp finish, biting finish, solvent finish, astringent finish, heavy finish, muted flavor, a solvent overtone in a peak or a finish, dry taste on a palate, a harsh peak that overshadows one or more flavors, bite, throat burn, bitterness, metallic taste, lingering aftertaste, cause of head motion, cause of involuntary physiological response, cause of gag reflex, and combinations thereof.

27. The method of claim 1, wherein the at least one unwanted congener includes ethyl acetate.

28. The method of claim 1, wherein removing the at least one unwanted congener includes preferentially removing the at least one unwanted congener relative to other congeners of a group of congeners from the pre-rehabilitated quantity of coffee.

29. The method of claim 1, wherein removing the at least one unwanted congener includes preferentially removing ethyl acetate relative to ethanol from the pre-rehabilitated quantity of coffee.

30. The method of claim 1 further comprising:

after preferentially removing the at least one unwanted congener, exposing the treated quantity of coffee to an inert atmosphere flush.

31. The method of claim 1 further comprising:

tilting the pressure-controllable environment, such that the pre-rehabilitated quantity of coffee is homogenously distributed within the pressure-controllable environment.

* * * * *